(12) United States Patent
Leigh

(10) Patent No.: US 12,115,348 B2
(45) Date of Patent: Oct. 15, 2024

(54) SELECTABLE DRUG DELIVERY RATE DEVICE

(71) Applicant: Cochlear Limited, Macquarie University (AU)

(72) Inventor: Charles Roger Leigh, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 851 days.

(21) Appl. No.: 17/265,071

(22) PCT Filed: Nov. 18, 2019

(86) PCT No.: PCT/IB2019/059891
§ 371 (c)(1),
(2) Date: Feb. 1, 2021

(87) PCT Pub. No.: WO2020/104918
PCT Pub. Date: May 28, 2020

(65) Prior Publication Data
US 2021/0244878 A1    Aug. 12, 2021

Related U.S. Application Data

(60) Provisional application No. 62/769,690, filed on Nov. 20, 2018.

(51) Int. Cl.
*A61M 5/168* (2006.01)
*A61M 5/142* (2006.01)
*A61M 39/24* (2006.01)

(52) U.S. Cl.
CPC .... *A61M 5/16827* (2013.01); *A61M 5/14276* (2013.01); *A61M 39/24* (2013.01)

(58) Field of Classification Search
CPC .............. A61M 5/16827; A61M 39/24; A61M 5/14276; A61M 2205/3507; A61M 2205/50; A61M 5/172; A61M 39/22
See application file for complete search history.

(56) References Cited

U.S. PATENT DOCUMENTS 3,951,147 A    4/1976   Tucker et al.
4,626,244 A   12/1986   Reinicke
(Continued)

FOREIGN PATENT DOCUMENTS

DE    19915201 A1 * 10/2000 ........ A61M 5/14276

OTHER PUBLICATIONS

Int'l Search Report and Written Opinion for PCT/IB2019/059891, mailed Feb. 20, 2020.

*Primary Examiner* — Michael J Tsai
*Assistant Examiner* — Rachel T. Smith
(74) *Attorney, Agent, or Firm* — Knobbe, Martens, Olson & Bear, LLP

(57) ABSTRACT

An apparatus is provided which includes a plurality of conduits and a plurality of valves in fluidic communication with the plurality of conduits. The plurality of conduits is configured to receive liquid from at least one liquid reservoir configured to be implanted on or within a recipient. Each conduit of the plurality of conduits has a corresponding flow resistance to the liquid. The plurality of valves is configured to controllably allow flow of the liquid through a selected set of the conduits to be administered internally to the recipient with a selected flow rate.

30 Claims, 13 Drawing Sheets

(56) References Cited

U.S. PATENT DOCUMENTS

| | | |
|---|---|---|
| 4,931,050 A | 6/1990 | Idriss |
| 6,203,523 B1 | 3/2001 | Haller et al. |
| 6,666,845 B2 | 12/2003 | Hooper et al. |
| 7,044,942 B2 | 5/2006 | Jolly et al. |
| 7,338,028 B2 | 3/2008 | Zimmerling et al. |
| 8,515,560 B2 | 8/2013 | Debruyne et al. |
| 8,750,988 B2 | 6/2014 | Jolly et al. |
| 9,101,732 B2 | 8/2015 | Dadd et al. |
| 9,162,009 B2 | 10/2015 | Rapsey et al. |
| 9,616,207 B2 | 4/2017 | Verhoeven et al. |
| 2005/0273081 A1 | 12/2005 | Olsen |
| 2008/0161741 A1 | 7/2008 | Bene et al. |
| 2009/0326517 A1 | 12/2009 | Bork et al. |
| 2011/0224629 A1 | 9/2011 | Jolly et al. |
| 2011/0319836 A1* | 12/2011 | Lee .................... F16K 11/0856 604/248 |
| 2014/0296784 A1* | 10/2014 | Lopez ................. A61M 5/1413 604/151 |
| 2017/0216516 A1* | 8/2017 | Dale .................... A61M 39/24 |
| 2017/0340485 A1 | 11/2017 | Verhoeven et al. |
| 2018/0147346 A1* | 5/2018 | Grosse-Wentrup .......................... A61M 5/14232 |

\* cited by examiner

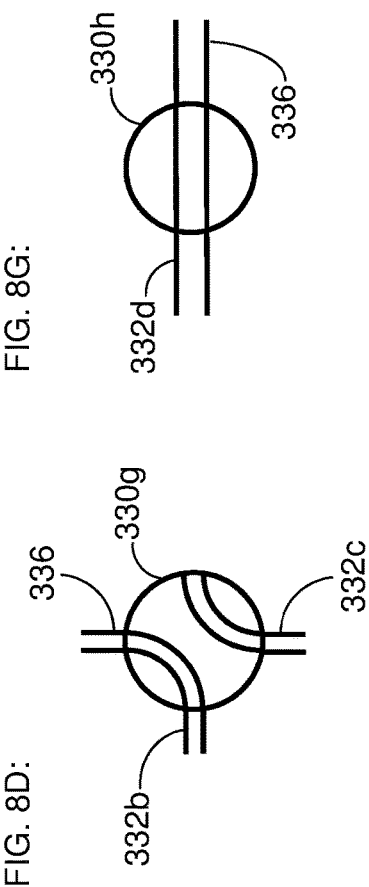
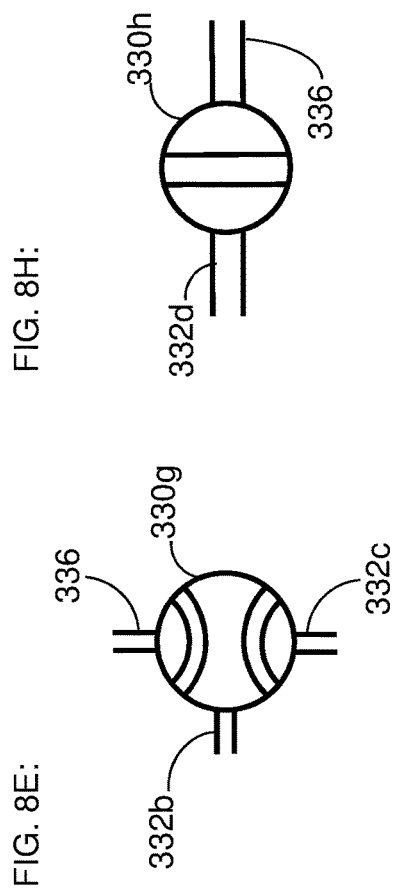
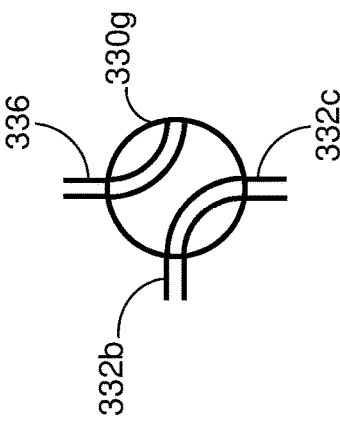
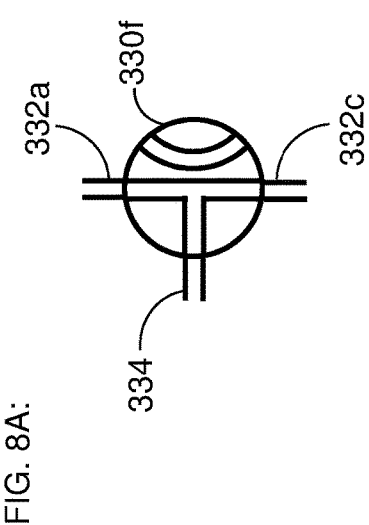
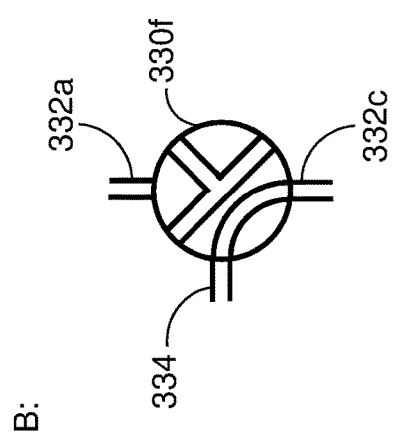
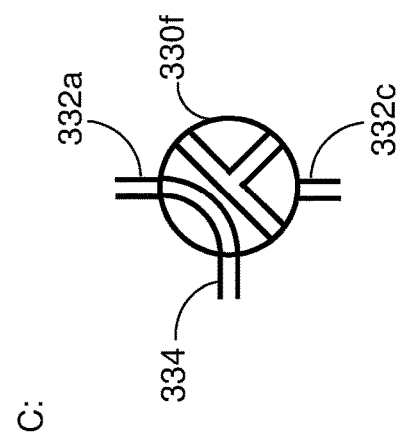

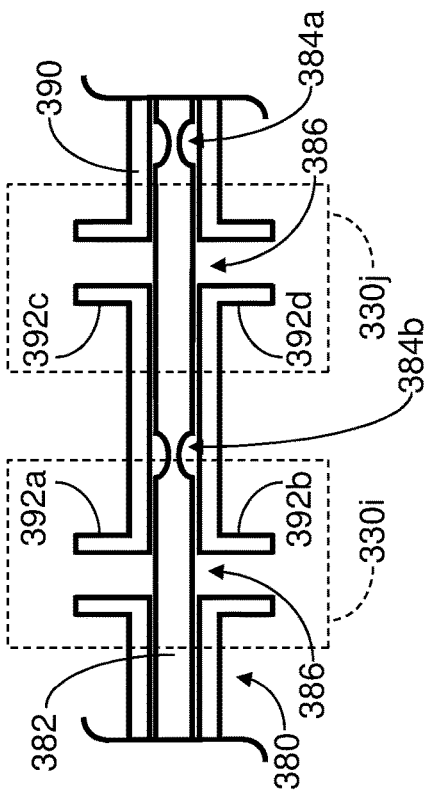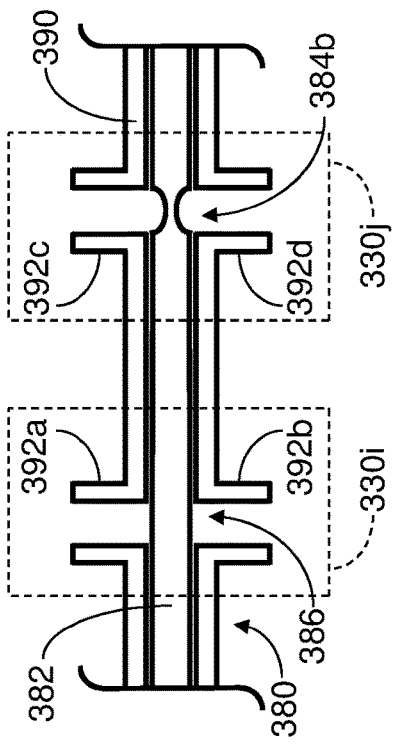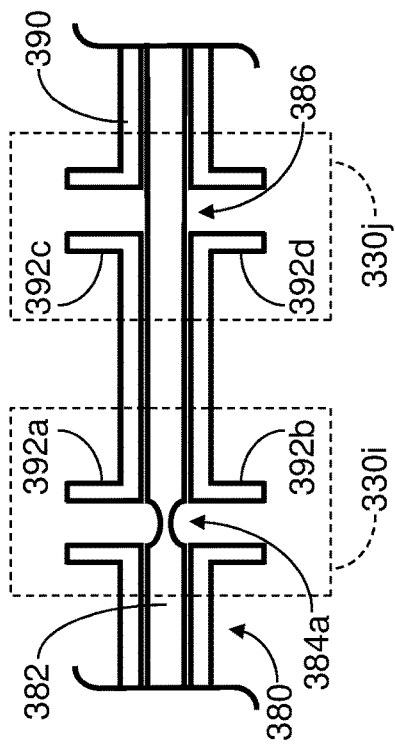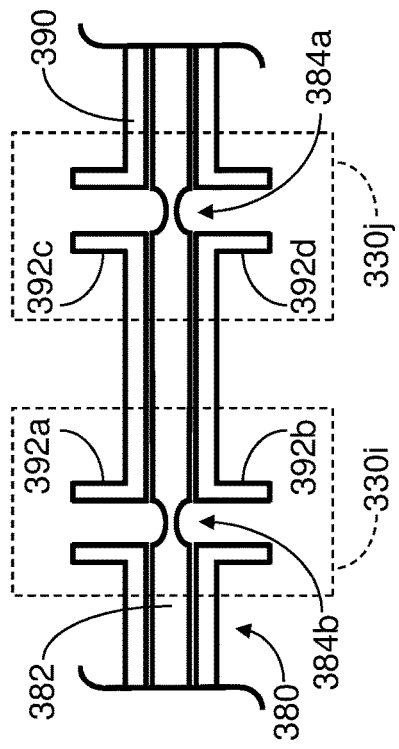

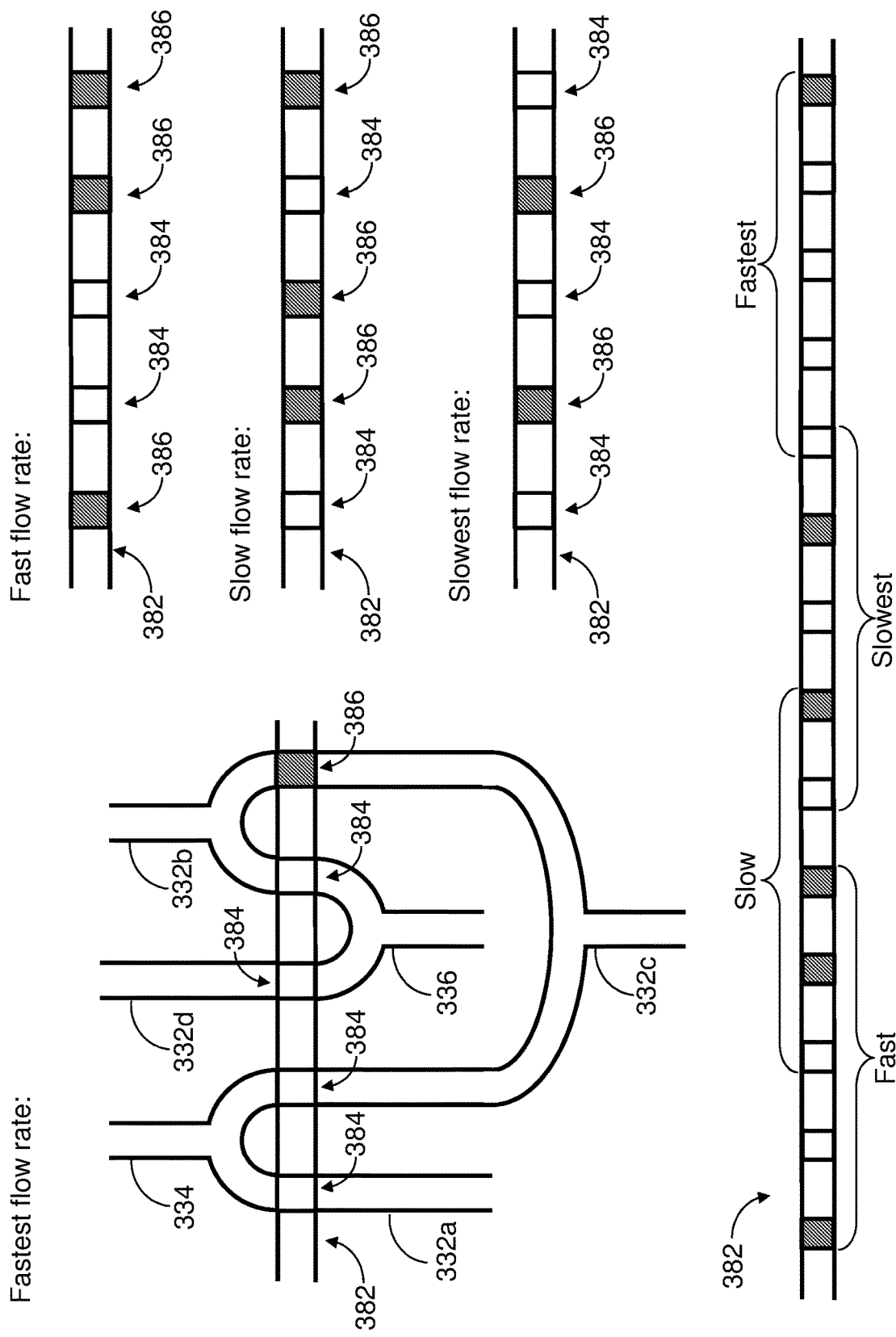

SELECTABLE DRUG DELIVERY RATE DEVICE

BACKGROUND

Field

This application is directed generally to implantable systems and methods for delivery of treatment substances to a recipient.

Description of the Related Art

Individuals suffer from a variety of hearing problems, such as tinnitus, Meniere's disease, vertigo, hearing loss, etc. Hearing loss, for example, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like).

SUMMARY

In one aspect described herein, an apparatus is provided which comprises a plurality of conduits and a plurality of valves in fluidic communication with the plurality of conduits. The plurality of conduits is configured to receive liquid from at least one liquid reservoir configured to be implanted on or within a recipient. Each conduit of the plurality of conduits has a corresponding flow resistance to the liquid. The plurality of valves is configured to controllably allow flow of the liquid through a selected set of the conduits to be administered internally to the recipient with a selected flow rate.

In another aspect disclosed herein, a method is provided which comprises selectively placing one or more fluid conduits of a plurality of fluid conduits in fluidic communication with at least one reservoir of a treatment liquid. The at least one reservoir is configured to be implanted on or within a recipient. The one or more fluid conduits are selected, at least in part, to provide a predetermined flow rate of the treatment liquid to the recipient. The method further comprises implanting the at least one reservoir and the plurality of fluid conduits on or within the recipient.

In another aspect disclosed herein, an apparatus is provided which comprises a housing configured to be implanted on or within a recipient. Within the housing, the apparatus further comprises at least one reservoir and a flow control system. The at least one reservoir is configured to contain a liquid. The flow control system comprises at least one input port configured to receive the liquid from the at least one reservoir, and at least one output port configured to administer the liquid internally to the recipient. The flow control system further comprises a plurality of flow restrictors each having a corresponding flow resistance to the liquid and a plurality of valves in fluidic communication with the plurality of flow restrictors. The plurality of valves is configured to controllably allow flow from the at least one input port, through a selected set of the flow restrictors, to the at least one output port.

In another aspect disclosed herein, an implantable flow restrictor is provided which comprises an inlet port, an outlet port, and a fluidic pathway that connects the inlet port to the outlet port, wherein the fluidic pathway comprises at least two conduits, and the implantable flow restrictor is configured to connect the at least two conduits in one of a plurality of configurations to set a flow resistance of the fluidic pathway.

In some embodiments, a first of the at least two configurations connects at least two conduits of the at least two conduits in series. In some embodiments, a second of the at least two configurations connects at least two conduits of the at least two conduits in parallel. In some embodiments, a first conduit of the at least two conduits has a first flow resistance, and a second conduit of the at least two conduits has a second flow resistance, and the second flow resistance is less than two-thirds of the first flow resistance.

BRIEF DESCRIPTION OF THE DRAWINGS

Embodiments are described herein in conjunction with the accompanying drawings, in which:

FIGS. 8D-8F schematically illustrate another example valve having three valve states in accordance with certain embodiments described herein;

FIGS. 8G-8H schematically illustrate an example valve having two valve states in accordance with certain embodiments described herein;

FIG. 9A-9D schematically illustrates an example pair of valves having a common actuator configured to be moved linearly to change a valve state of each of the two valves in accordance with certain embodiments described herein;

FIG. 10 schematically illustrates an example plurality of valves comprising five valves with a common linear actuator in accordance with certain embodiments described herein.

DETAILED DESCRIPTION

Certain embodiments described herein advantageously provide an implantable drug delivery device configured to administer a liquid drug to the recipient with a selectable flow rate. The device utilizes two or more flow restrictors (e.g., having different flow resistances) and a plurality of valves configured to allow liquid flow from a reservoir to the recipient by flowing through a single selected flow restrictor or multiple selected flow restrictors, in series and/or in parallel with one another, to provide a desired liquid flow rate to the recipient.

Figure 1:
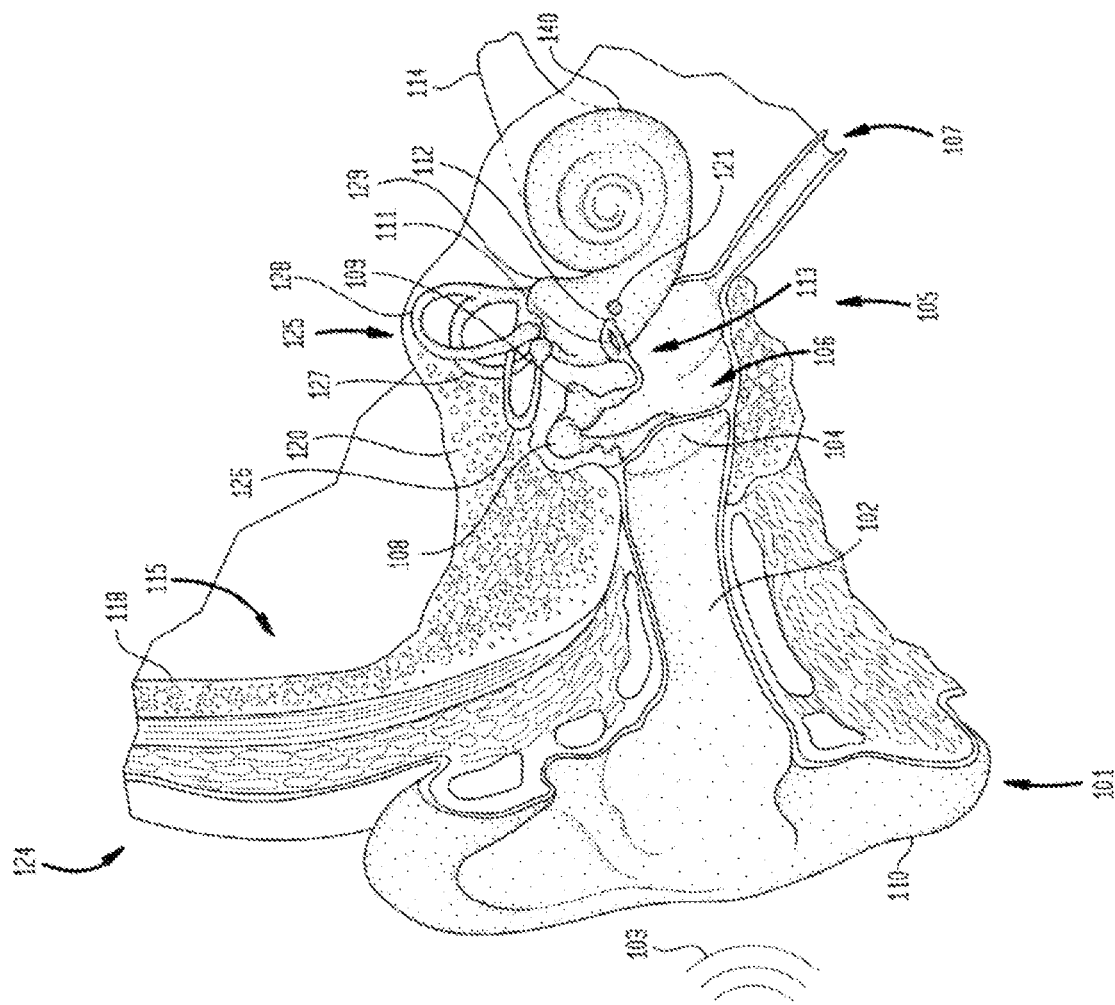
FIG. 1 is a schematic diagram illustrating the human anatomy of a recipient's ear.

Before describing illustrative embodiments of the treatment substance delivery systems and methods presented herein, a brief description of the human anatomy of a recipient's ear is first provided with reference to FIG. 1. As shown in FIG. 1, a recipient's ear comprises an outer ear 101, a middle ear 105, and an inner ear 107. In a fully functional ear, the outer ear 101 comprises an auricle 110 and an ear canal 102. An acoustic pressure or sound wave 103 is collected by the auricle 110 and channeled into and through the ear canal 102. Disposed across the distal end of the ear canal 102 is a tympanic membrane 104 which vibrates in response to sound wave 103. This vibration is coupled to the oval window or fenestra ovalis 112, which is adjacent the round window 121, through the bones of the middle ear 105. The bones of the middle ear 105 comprise the malleus 108, the incus 109, and the stapes 111, collectively referred to as the ossicles 106. The ossicles 106 are positioned in the middle ear cavity 113 and serve to filter and amplify the sound wave 103, causing the oval window 112 to articulate (vibrate) in response to the vibration of the tympanic membrane 104. This vibration of the oval window 112 sets up waves of fluid motion of the perilymph within the cochlea 140. Such fluid motion, in turn, activates tiny hair cells (not shown) inside of the cochlea 140. Activation of the hair cells causes appropriate nerve impulses to be generated and transferred through the spiral ganglion cells (not shown) and the auditory nerve 114 to the brain (also not shown) where they are perceived as sound.

The human skull is formed from a number of different bones that support various anatomical features. Illustrated in FIG. 1 is the temporal bone 115 which is situated at the side and base of the recipient's skull 124. For ease of reference, the temporal bone 115 is referred to herein as having a superior portion 118 and a mastoid portion 120. The superior portion 118 comprises the section of the temporal bone 115 that extends superior to the auricle 110. That is, the superior portion 118 is the section of the temporal bone 115 that forms the side surface of the skull. The mastoid portion 120, referred to herein simply as the mastoid 120, is positioned inferior to the superior portion 118. The mastoid 120 is the section of the temporal bone 115 that surrounds the middle ear 105.

As shown in FIG. 1, semicircular canals 125 are three half-circular, interconnected tubes located adjacent the cochlea 140. Vestibule 129 provides fluid communication between the semicircular canals 125 and the cochlea 140. The three canals 125 are the horizontal semicircular canal 126, the posterior semicircular canal 127, and the superior semicircular canal 128. The canals 126, 127, 128 are aligned approximately orthogonally to one another. Specifically, the horizontal canal 126 is aligned roughly horizontally in the head, while the superior canal 128 and the posterior canal 127 are aligned roughly at a 45 degree angle to a vertical through the center of the individual's head.

Each canal is filled with a fluid called endolymph and contains a motion sensor with tiny hairs (not shown) whose ends are embedded in a gelatinous structure called the cupula (also not shown). As the orientation of the skull changes, the endolymph is forced into different sections of the canals. The hairs detect when the endolymph passes thereby, and a signal is then sent to the brain. Using these hair cells, the horizontal canal 126 detects horizontal head movements, while the superior canal 128 and the posterior canal 127 detect vertical head movements.

In the treatment of various maladies, it can be advantageous to have an extended delivery solution for use in the delivery of treatment substances (e.g., medicine; drugs) to a target location of a recipient. In general, extended treatment substance delivery refers to the delivery of treatment substances over a period of time (e.g., continuously, periodically, etc.) and can be achieved using an implantable device which controllably provides the treatment substance to the recipient. The extended delivery can be activated during or after surgery and can be extended as long as is needed. The period of time can immediately follow the initial implantation of the implantable device or there can be a time period between initial implantation and subsequent activation of the delivery device. Certain embodiments described herein include features that facilitate controlled extended delivery of treatment substances. For example, certain embodiments are directed to apparatuses, systems, and methods for extended delivery of treatment substances in a controlled manner to deliver the treatment substances to a target location with a selected flow rate.

Figure 2A:
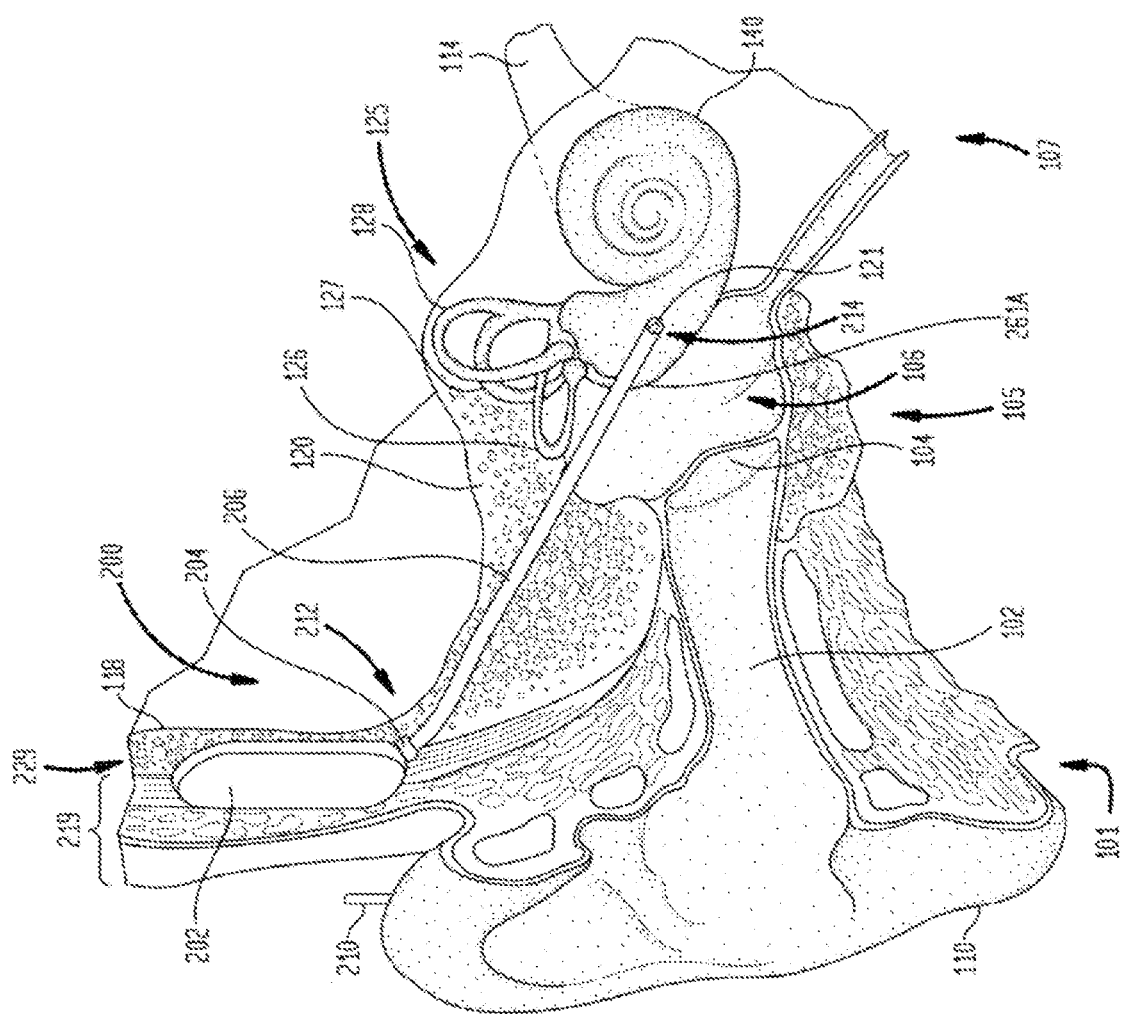
FIG. 2A illustrates an example implantable delivery system in accordance with certain embodiments described herein.
Figure 2B:
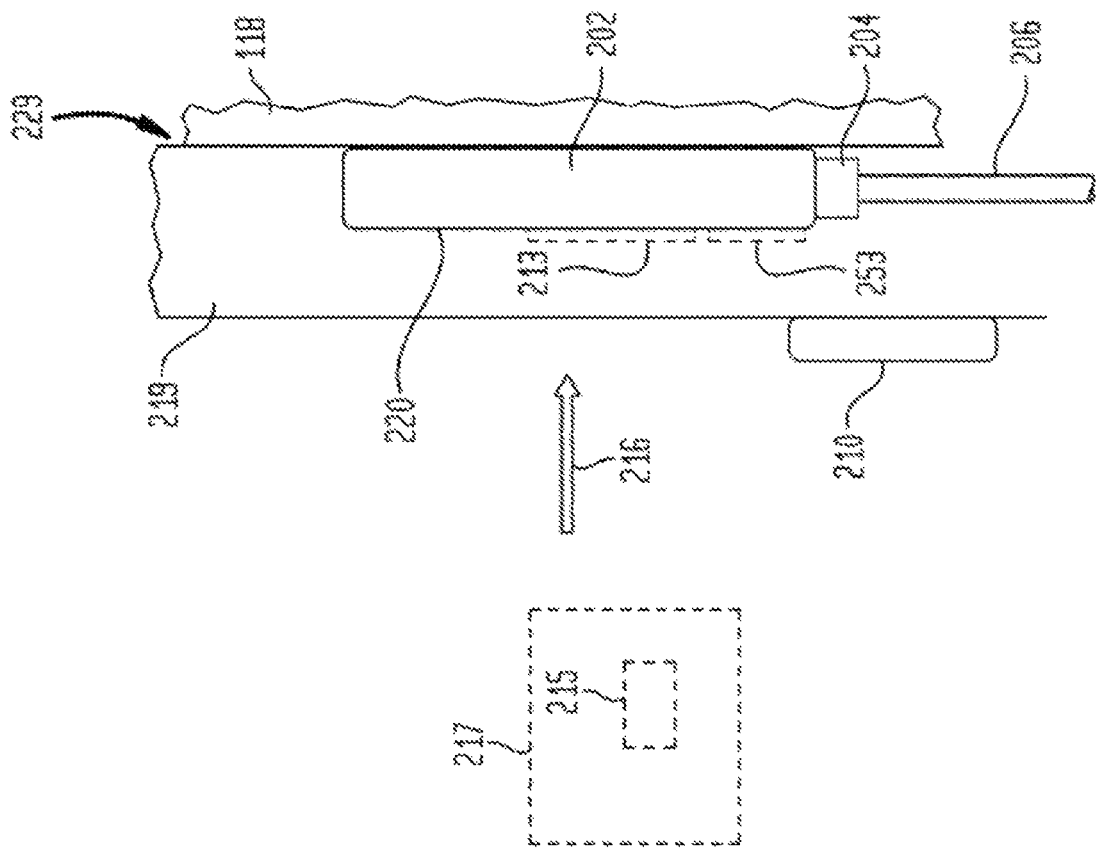
FIG. 2B illustrates a first portion of the example delivery system of FIG. 2A.
Figure 2C:
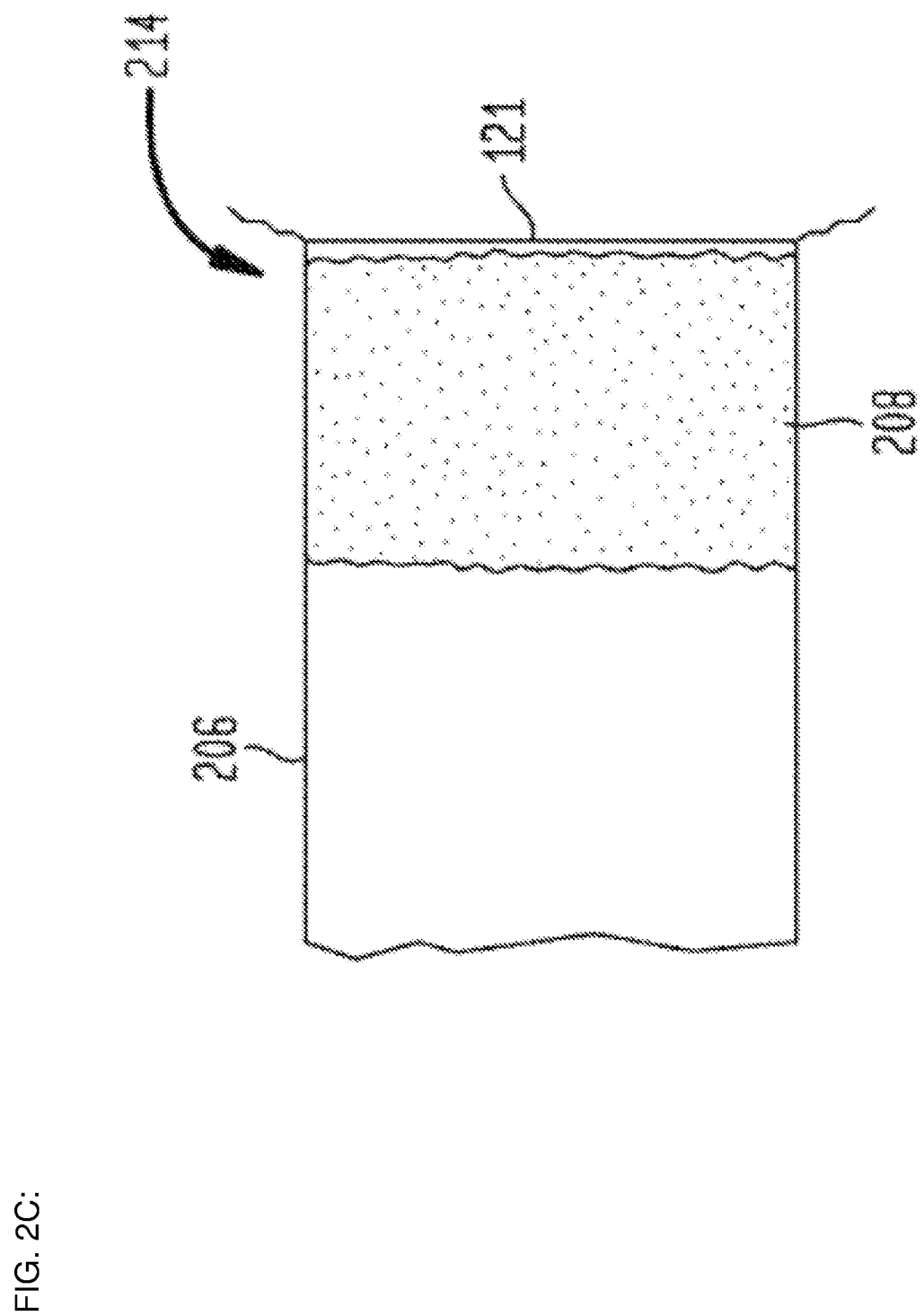
FIG. 2C is a cross-sectional view of a second portion of the example delivery system of FIG. 2A.

FIG. 2A illustrates an example implantable delivery system 200 in accordance with certain embodiments described herein. The example delivery system 200 of FIG. 2A is sometimes referred to herein as an inner ear delivery system because it is configured to deliver treatment substances to the recipient's inner ear (e.g., the target location is the interior of the recipient's cochlea 140). FIG. 2B illustrates a first portion of the example delivery system 200 of FIG. 2A, and FIG. 2C is a cross-sectional view of a second portion of the example delivery system 200 of FIG. 2A. While FIGS. 2A-2C illustrate an example implantable delivery system 200 configured to administer at least one treatment substance to the inner ear of the recipient (e.g., to the round window 121), the implantable delivery system of certain other embodiments is configured to administer at least one treatment substance to other portions of the recipient's body (e.g., bones; spine; organs; heart; lungs; liver; brain; stomach; pancreas; kidneys; eyes).

The example delivery system 200 of FIGS. 2A-2C comprises at least one reservoir 202, at least one valve 204, at least one delivery tube 206, and at least one delivery device 208. As shown in FIGS. 2A-2B, the example delivery system 200 includes, or is configured to be operated with, an external magnet 210. For ease of illustration, the example delivery system 200 of FIGS. 2A-2C is shown separate from any implantable auditory prostheses. However, in certain embodiments, the example delivery system 200 is configured to be used with, for example, cochlear implants, direct acoustic stimulators, bone conduction devices, etc. In certain such embodiments, the implantable components (e.g., reservoir 202, valve 204, delivery tube 206, etc.) of the delivery system 200 can be separate from other components of the implantable auditory prosthesis, while in certain other such embodiments, the implantable components of the delivery system 200 are integrated with the other components of the implantable auditory prosthesis.

As illustrated by FIGS. 2A-2B, in certain embodiments, the reservoir 202 is positioned within the recipient underneath a portion of the recipient's skin/muscle/fat, collectively referred to herein as tissue 219. For example, the reservoir 202 can be positioned between layers of the recipient's tissue 219 or adjacent to a subcutaneous outer surface 229 of the recipient's skull (e.g., positioned in a surgically created pocket at the outer surface 229 adjacent to a superior portion 118 of the temporal bone 115). The reservoir 202 of certain embodiments is, prior to or after implantation, at least partially filled with a treatment substance for delivery to the inner ear 107 of the recipient. The treatment substance can be, for example, in a liquid form, a gel form, and/or comprise nanoparticles or pellets. In certain embodiments, the treatment substance can initially be in a crystalline/solid form that is subsequently dissolved. For example, the reservoir 202 can include two chambers, one that comprises a fluid (e.g., artificial perilymph or saline) and one that comprises the crystalline/solid treatment substance. The fluid can be mixed with the crystalline/solid treatment substance to form a fluid or gel treatment substance that can be subsequently delivered to the recipient.

In certain embodiments, the reservoir 202 includes a needle port (not shown) so that the reservoir 202 can be refilled via a needle injection through the skin. In certain other embodiments, the reservoir 202 is explanted and replaced with another reservoir that is, prior to or after implantation, at least partially filled with a treatment substance. In certain embodiments, the reservoir 202 has a preformed shape and is implanted in this shape. In certain other embodiments, the reservoir 202 has a first shape that facilitates implantation and a second shape for use in delivering treatment substances to the recipient. For example, the reservoir 202 can have a rolled or substantially flat initial shape that facilitates implantation, and the reservoir 202 can be configured to then expand after implantation. Certain such embodiments can be used, for example, to insert the reservoir 202 through a tympanostomy into the middle ear 105 or the ear canal 102, through an opening in the inner ear 107, or to facilitate other minimally invasive insertions.

In certain embodiments, the reservoir 202 includes a notification mechanism (not shown) that transmits a signal or notification indicating that the reservoir 202 is substantially empty and/or needs to be refilled or replaced. For example, one or more electrode contacts (not shown) can be present and become electrically connected when the reservoir 202 is substantially empty. Electronic components associated with or connected to the reservoir 202 can accordingly transmit a signal indicating that reservoir 202 needs to be refilled or replaced.

In certain embodiments, the at least one valve 204 is positioned between the at least one reservoir 202 and the at least one delivery tube 206, is in fluidic communication with the at least one reservoir 202 and the at least one delivery tube 206, and is configured to control flow of the treatment substance from the at least one reservoir 202 to the recipient via the at least one delivery tube 206. In certain embodiments, the at least one valve 204 comprises a check valve (e.g., one-way valve) configured to allow the treatment substance to pass through the check valve in one direction only so that the released treatment substances do not backflow into the reservoir 202. In certain embodiments, the at least one valve 204 comprises a valve that is configured to open in response to the pressure change in the reservoir 202 (e.g., ball check valve, diaphragm check valve, swing check valve, tilting disc check valve, etc.). In certain embodiments, the at least one valve 204 comprises a stop-check valve that can be controllably opened or closed (e.g., by an external mechanism; by a controller of an implanted portion of the delivery system 200) to control the flow regardless of forward pressure. For example, the stop-check value can be controlled by an external electric or magnetic field generated by the external magnet 210, an electromagnet, etc. The valve 204 of FIGS. 2A and 2B is temporarily open when the external magnet 210 is positioned in proximity to the valve 204 and is closed when the external magnet 210 is removed from the proximity of the valve 204. In certain embodiments, variable strengths of the magnetic field (e.g., variable external magnet strengths; adjustable strength of an electromagnet) are used to control the valve 204 and therefore the dosage of the treatment substance. The stop-check valve of certain embodiments includes an override control to stop flow regardless of flow direction or pressure, as well as closing in response to backflow or insufficient forward pressure (e.g., as in a normal check valve). In certain embodiments, the stop-check valve is configured to prevent unintended dosing of the treatment substance when, for example, an accidental external force acts on the reservoir 202. The reservoir 202 is formed such that an increase in pressure of the reservoir 202 without an accompanying treatment substance release will not damage (e.g., rupture) the reservoir 202.

The use of a magnetically activated stop-check valve is merely exemplary and other types of valves can be used in accordance with certain embodiments described herein. For example, the at least one valve 204 can be actuated (e.g., opened) in response to an electrical signal (e.g., piezoelectric valve). In certain such embodiments, the electrical signal is received from a portion of an auditory prosthesis (not shown) that is implanted with the delivery system 200 or the electrical signal is received from an external device (e.g., an RF actuation signal received from an external sound processor, remote control, etc.). In certain other embodiments, the at least one valve 204 is actuated manually (e.g., by a force applied by a finger).

In certain embodiments, the delivery tube 206 includes a proximal end 212 and a distal end 214. The proximal end 212 of the delivery tube 206 is in fluidic communication with the at least one valve 204 through which the treatment substance is controllably released from the reservoir 202. As shown in FIG. 2C, the distal end 214 of the delivery tube 206 comprises a delivery device 208 which, in certain embodiments, is disposed within the distal end 214 of the delivery tube 206, positioned abutting the round window 121, and configured to be in fluidic communication with the recipient's round window 121. For example, the delivery tube 206 can be secured within the recipient so that the distal end 214 remains located adjacent to the round window 121. In certain embodiments, the delivery device 208 (e.g., wick, sponge, permeating gel, hydrogel; non-return valve) is configured to operate as a transfer mechanism to transfer the treatment substance from the delivery tube 206 to the recipient. For example, the delivery device 208 can be in fluidic communication with the round window 121 such that once the treatment substance is released through the valve 204, the treatment substance flows through the delivery tube 206 to the delivery device 208, and enters the cochlea 140 through the round window 121 (e.g., via osmosis).

In certain embodiments, the example delivery system 200 comprises an active actuation mechanism (e.g., a pump) configured to transfer the at least one treatment substance from the at least one reservoir 202 to the recipient via the at least one delivery device 208 at the distal end 214 of the at least one delivery tube 206. For example, the example delivery system 200 can comprise a mechanism (e.g., at least one spring) configured to controllably apply a force to at least one compressible part or portion of the reservoir 202 (e.g., a wall 220 or a portion thereof, formed from a resiliently flexible material) so as to propel (e.g., push) a portion of the treatment substance out of the reservoir 202 through the valve 204 (e.g., via peristaltic pumping). Certain embodiments described herein utilize an actuation mechanism that is controlled externally or electronically (e.g., to selectively pump or not, thereby controlling the flow rate by modifying a duty cycle of the actuation mechanism), and the delivery system 200 provides an alternative ability of controlling the flow rate. In certain other embodiments, the actuation mechanism is self-actuating (e.g., without external control) and the delivery system 200 provides the sole ability of controlling the flow rate. For example, for an actuation mechanism actuated by a phase material change (e.g., two chambers separated by a deformable membrane within the implant body, one chamber with a phase change material and the other chamber containing the treatment material), there is no control of the flow rate except as provided by the delivery system 200.

In certain other embodiments, the example delivery system 200 utilize a passive actuation mechanism configured to transfer the at least one treatment substance from the at least one reservoir 202 to the recipient via the at least one delivery device 208 at the distal end 214 of the at least one delivery tube 206. For example, as illustrated in FIGS. 2A and 2B, the reservoir 202 can be positioned adjacent to the outer surface 229 of the recipient's skull so that an external force 216 can be applied to a compressible part or portion of the reservoir 202 (e.g., a wall 220 or a portion thereof, formed from a resiliently flexible material) which can be configured to deform in response to application of the external force 216 to propel (e.g., push) the treatment substance from the reservoir 202. In certain embodiments, the positioning of the reservoir 202 adjacent to the superior portion 118 of the mastoid 115 provides a rigid surface that counters the external force 216. As a result, a pressure change occurs in the reservoir 202 so as to propel (e.g., push) a portion of the treatment substance out of the reservoir 202 through the valve 204.

FIG. 2B illustrates an example arrangement in which the reservoir 202 includes a resiliently flexible wall 220, which can be formed from various resiliently flexible parts and rigid parts and which can have a variety of shapes and sizes (e.g., cylindrical, square, rectangular, etc.) or other configurations. For example, the reservoir 202 can further include a spring-mounted base that maintains a pressure in the reservoir 202 until the reservoir 202 is substantially empty. Other mechanisms for maintaining a pressure in the reservoir can be used in other arrangements.

In certain embodiments, the external force 216 is applied manually using, for example, a user's finger. The user (e.g., recipient, clinician, caregiver, etc.) can press on the tissue 219 adjacent to the reservoir 202 to create the external force 216. In certain embodiments, a single finger press is sufficient to propel the treatment substance through valve 204. In certain other embodiments, multiple finger presses are used to create a pumping action that propels the treatment substance from the reservoir 202. In certain embodiments, the external force 216 is applied through a semi-manual method that uses an external actuator 217, as shown in FIG. 2B. For example, the external actuator 217 can be pressed onto the soft tissue 219 under which the reservoir 202 is located. The movement (e.g., oscillation/vibration) of the actuator 217 deforms the reservoir 202 to create the pumping action that propels the treatment substance out of the reservoir 202.

In certain embodiments, the force applied to the reservoir 202 to propel the treatment substance from the reservoir 202 is generated by a recipient's muscle (e.g., temporalis, temporal muscle, jaw, etc.) and hard tissue (e.g., bone, teeth, etc.). The muscle (not shown) can be in a relaxed state where little or no pressure is placed on the reservoir 202 or alternatively can be in a contracted state that compresses the reservoir 202. The compression of the reservoir 202 in response to the muscle contraction propels the treatment substance from the reservoir 202 into the delivery tube 206 via the valve 204. In certain embodiments, the muscle can be contracted through mastication.

In certain embodiments, internal and/or external magnets and/or magnetic materials are used in the arrangements of FIG. 2B to ensure that the actuator 217 applies force at an optimal location of the reservoir 202. For example, the reservoir 202 can include a magnetic positioning member 213 located at or near an optimal location for application of an external force from the actuator 217. The actuator 217 can include a magnet 215 configured to magnetically mate with the magnetic positioning member 213. As such, when the actuator 217 is properly positioned, the magnet 215 mates with the magnetic positioning member 213 and the force from the actuator 217 is applied at the optimal location.

In certain embodiments, the example delivery system 200 comprises a controller (e.g., implanted electronics 253, shown using dotted lines in FIG. 2B) configured to be in communication with an actuator (e.g., active or passive actuation mechanism) and/or the valve 204. For example, the implanted electronics 253 can be configured to control the actuation mechanism and/or the valve 204 to control the release of the treatment substance from the reservoir 202 to the recipient. In certain embodiments, the implanted electronics 253 is powered and/or controlled through a transcutaneous link (e.g., RF link). For example, the implanted electronics 253 can include or be electrically connected to an RF coil, receiver/transceiver unit, etc.

In certain embodiments, the implanted electronics 253 includes or is connected to at least one sensor that is configured, at least in part, to assist in control of delivery of the treatment substance to the recipient. For example, the at least one sensor (e.g., a temperature sensor, a sensor to detect infection or bacteria growth, etc.) can provide indications of conditions under which delivery of the treatment substance is to occur (e.g., for a period of time) and/or conditions under which delivery of the treatment substance is to be ceased (e.g., for a period of time). The at least one sensor can also be configured to determine an impact of the treatment substance on the recipient (e.g., evaluate effectiveness of the treatment substance).

Figure 3A:
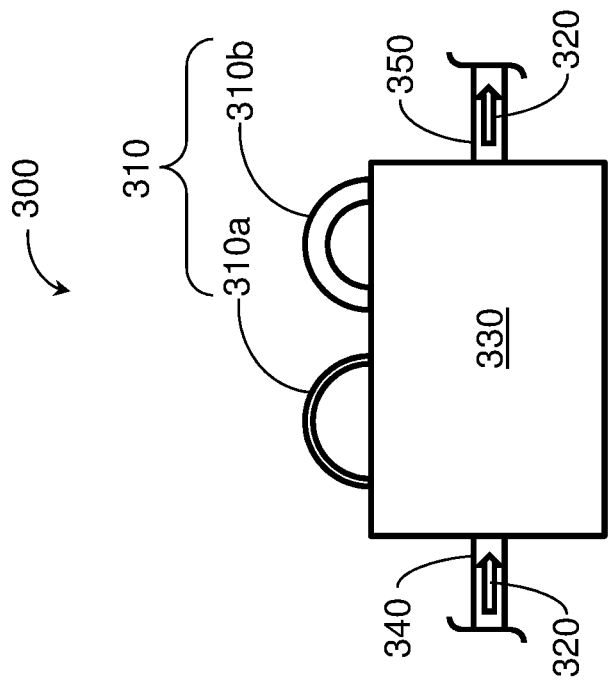
FIGS. 3A and 3B schematically illustrate two example apparatus in accordance with certain embodiments described herein.
Figure 3B:
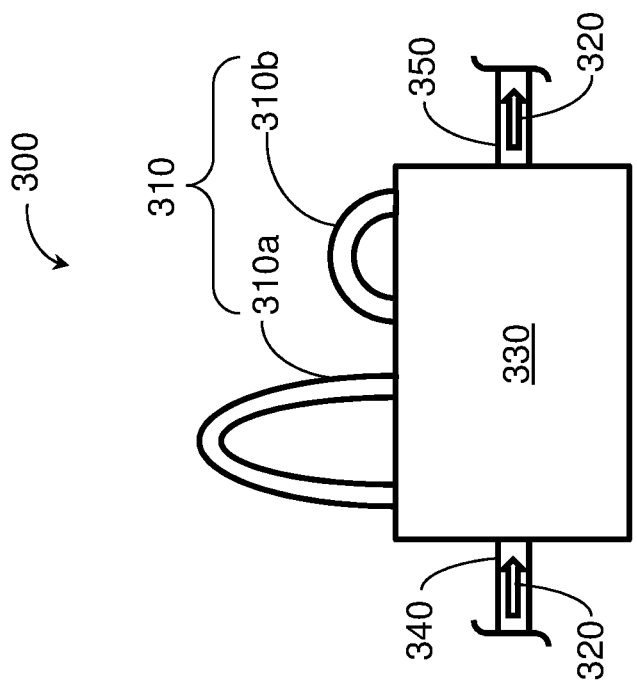

FIGS. 3A and 3B schematically illustrate two example apparatus 300 in accordance with certain embodiments described herein. The apparatus 300 comprises a plurality of conduits 310 configured to receive liquid 320 from at least one liquid reservoir 202 (not shown in FIGS. 3A and 3B) configured to be implanted on or within a recipient. Each conduit 310 of the plurality of conduits 310 has a corresponding flow resistance to the liquid 320. The apparatus 300 further comprises a plurality of valves 330 in fluidic communication with the plurality of conduits 310. The plurality of valves 330 is configured to controllably allow flow of the liquid 320 through a selected set of the conduits 310 to be administered internally to the recipient with a selected flow rate. For example, the selected set can comprise a single selected conduit 310 of the plurality of conduits 310 or can comprise multiple selected conduits 310 of the plurality of conduits 310, with two or more of the selected conduits 310 in series with one another and/or with two or more of the selected conduits 310 in parallel with one another.

As schematically illustrated by FIGS. 3A and 3B, the plurality of conduits 310 of certain embodiments comprises two conduits 310, a first conduit 310*a* and a second conduit 310*b*. Other numbers of conduits 310 (e.g., 2, 3, 4, 5, or more) are also compatible with certain embodiments described herein. The conduits 310 of certain embodiments comprise tubular structures (e.g., capillary tubing of plastic, rubber, and/or metal such as steel), such as have been used in implantable infusion pumps, each having an inlet portion and an outlet portion. For example, one or more of the conduits 310 can comprise a spiral-shaped flow restrictor, having its inlet portion in fluidic communication with the plurality of valves 330 and its outlet portion in fluidic communication with the plurality of valves 330. Other examples of conduits 310 include, but are not limited to, grooves or channels etched into a structure (e.g., plate; glass; silica chip), fluid pathways formed in a molded or vapor deposited component (e.g., silicone; parylene), needle restrictors, channel restrictors, orifice plate restrictors, and other flow restrictors that have been used in implantable infusion pumps.

In certain embodiments, the flow resistance of each conduit 310 is different from the flow resistance of each of the other conduits 310, while in certain other embodiments, the flow resistances of two or more of the conduits 310 are equal to one another. The flow resistance of a conduit 310 is dependent at least in part upon structural characteristics of the conduit 310. For example, referring to FIGS. 3A and 3B, the first conduit 310*a* has a first flow resistance dependent at least in part upon structural characteristics of the first conduit 310*a*, and the second conduit 310*b* has a second flow resistance dependent at least in part upon structural characteristics of the second conduit 310*b*, with the second flow resistance lower than the first flow resistance. In certain embodiments, the flow resistance of a conduit 310 can be expressed as the pressure difference of the liquid 320 between the inlet portion and the outlet portion divided by the flow rate of the liquid 320 through the conduit 310. Using the Poisseuille equation, the flow resistance R of an example conduit 310 having an inner passageway with a uniform circular cross-section can be expressed as:

$$R = \frac{\Delta P}{Q} \propto \frac{\mu L}{r^4}$$

where Q is the flow rate (ml/sec), $\Delta P$ is the liquid pressure differential (dynes/cm$^2$) between the inlet portion and the outlet portion, r is the inner radius (cm) of the conduit 310, p is the viscosity (poise) of the liquid 320, and L is the length (cm) of the conduit 310 from the inlet portion to the outlet portion. In certain embodiments, the lengths L of the conduits 310 can range from 15 cm to 30 m and the inner dimensions (e.g., radii; diameters; widths) of the passageways (e.g., having circular, square, rectangular, or other geometric or non-geometrical cross-sectional shapes) of the conduits 310 can range from 5 µm to 50 µm. The inner dimensions of the passageway of the conduit 310 in certain embodiments is generally uniform along the length of the conduit 310, while in certain other embodiments, the inner dimensions are non-uniform along the length of the conduit 310.

FIG. 3A schematically illustrates the first conduit 310*a* and the second conduit 310*b* having different lengths L, with the first conduit 310*a* longer than the second conduit 310*b* and the first flow resistance higher than the second flow resistance. FIG. 3B schematically illustrates the first conduit 310*a* and the second conduit 310*b* having different inner dimensions (e.g., inner radii r), with the passageway of the first conduit 310*a* narrower than the passageway of the second conduit 310*b* and the first flow resistance higher than the second flow resistance. In certain other embodiments, the conduits 310 have both differing lengths and differing inner dimensions such that the flow resistances of the conduits 310 differ from one another.

In certain embodiments, the liquid 320 comprises one or more treatment substances (e.g., medicines; drugs; pharmaceutical compositions; genetic materials having a direct or indirect genetic therapeutic effect; biologic substances that comprise living matter or are derived from living matter intended to have a therapeutic effect; antispasmodics; anti-inflammatories; anti-cancer or chemotherapeutic agents; analgesic pain control medications; insulin; steroids) which can be, for example, in a liquid form, a gel form, and/or comprise nanoparticles or pellets. In certain embodiments, the liquid 320 comprises a solvent or carrier liquid (e.g., water; saline; artificial perilymph) in which the treatment substance is dissolved, suspended, or mixed (e.g., prior to placing the liquid 320 within the reservoir 202 or immediately prior to flowing the liquid 320 through the plurality of valves 330) and subsequently delivered to the recipient.

Figure 4:
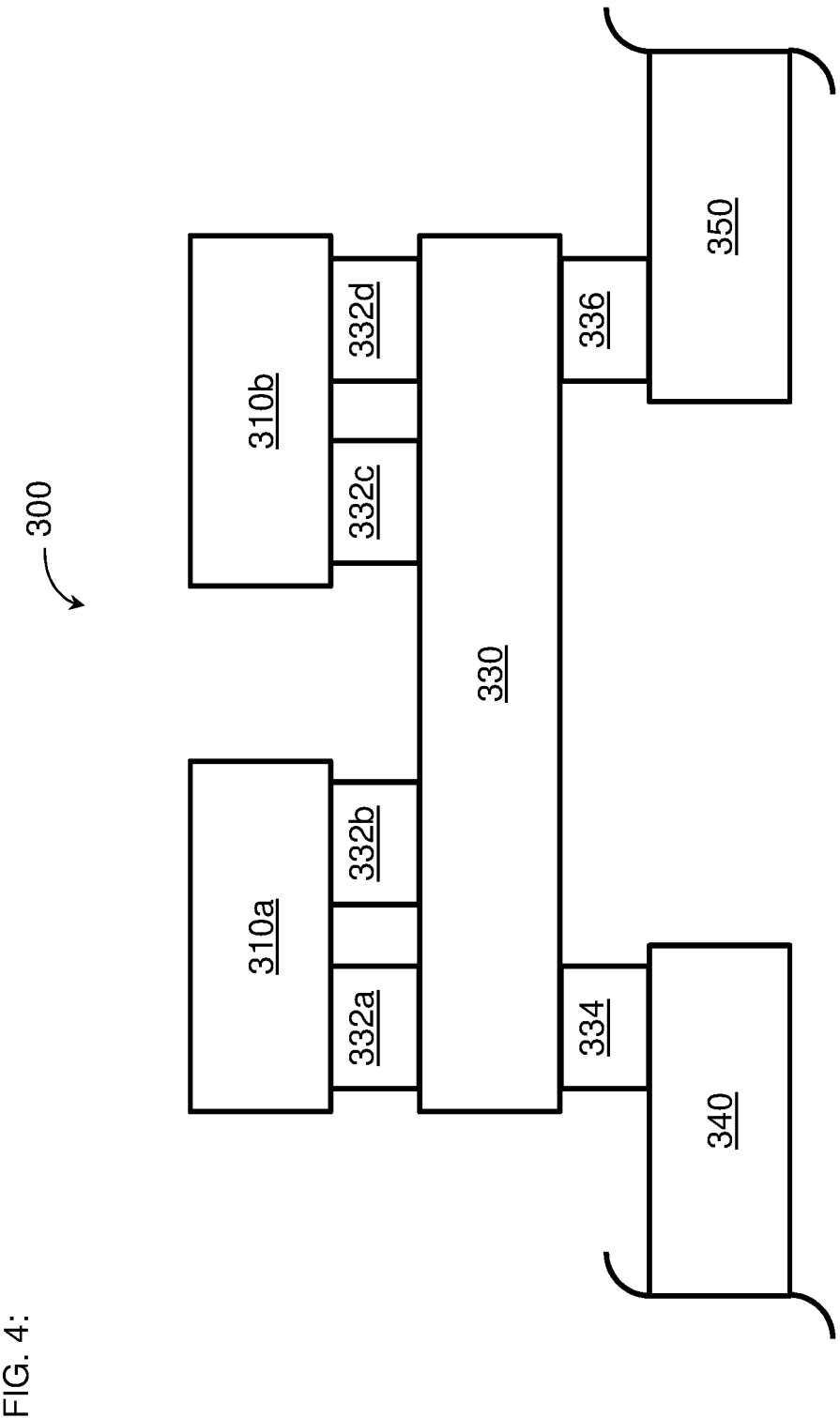
FIG. 4 schematically illustrates an example apparatus having a first conduit and a second conduit in fluidic communication with a plurality of valves in accordance with certain embodiments described herein.

FIG. 4 schematically illustrates an example apparatus 300 having a first conduit 310*a* and a second conduit 310*b* in fluidic communication with a plurality of valves 330 in accordance with certain embodiments described herein. The plurality of valves 330 comprises a first port 332*a* in fluidic communication with an inlet portion of the first conduit 310*a*, a second port 332*b* in fluidic communication with an outlet portion of the first conduit 310*a*, a third port 332*c* in fluidic communication with an inlet portion of the second conduit 310*b*, and a fourth port 332*d* in fluidic communication with an outlet portion of the second conduit 310*b*. The plurality of valves 330 further comprises an inlet port 334 in fluidic communication with an inlet conduit 340 which is in fluidic communication with at least one reservoir 202 (not shown in FIG. 4) and an outlet port 336 in fluidic communication with an outlet conduit 350 (e.g., a delivery tube 206) in fluidic communication with a target region of the recipient at which the liquid 320 comprising the treatment substance is to be administered.

In certain embodiments, the plurality of valves 300 is configured to be placed in a selected state of a plurality of states. FIGS. 5A-5D schematically illustrate four states of a plurality of states in accordance with certain embodiments described herein. In a first state, schematically illustrated by FIG. 5A, the plurality of valves 300 allows flow of the liquid 320 through the first conduit 310a and the second conduit 310b in series with one another. In a second state, schematically illustrated by FIG. 5B, the plurality of valves 300 allows flow of the liquid 320 through the first conduit 310a and does not allow flow of the liquid 320 through the second conduit 310b. In a third state, schematically illustrated by FIG. 5C, the plurality of valves 300 allows flow of the liquid 320 through the second conduit 310b and does not allow flow of the liquid 320 through the first conduit 310a. In a fourth state, schematically illustrated by FIG. 5D, the plurality of valves 300 allows flow of the liquid through the first conduit 310a and the second conduit 310b in parallel with one another. In certain embodiments, the plurality of states comprises a fifth state in which the plurality of valves 330 does not allow flow of the liquid 320 through either the first conduit 310a or the second conduit 310b.

In each of the first state, second state, third state, and fourth state, the liquid 320 flows through the apparatus 300 (e.g., from the inlet conduit 340, through the outlet conduit 350, to the recipient) with a flow rate Q that is dependent on the state of the plurality of valves 330. In certain embodiments, the first flow resistance $R_1$ of the first conduit 310a is higher than the second flow resistance $R_2$ of the second conduit 310b ($R_1 > R_2$), so for the same pressure differential $\Delta P$ between the inlet port 334 and the outlet port 336, the flow rates $Q_1$, $Q_2$, $Q_3$, and $Q_4$ of the apparatus 300 with the plurality of valves 300 in the first state, second state, third state, and fourth state, respectively, have the following relationship: $Q_4 > Q_3 > Q_2 > Q_1$. In certain embodiments, each of the conduits 310 is configured to have a corresponding flow resistance such that the flow rates for the states of the plurality of valves 330 are differentiated from one another. For example, for a first flow resistance $R_1$ of the first conduit 310a equal to twice the second flow resistance $R_2$ of the second conduit 310b ($R_1 = 2R_2$), the flow rates in the first state, second state, third state, and fourth state are $$Q_4 = \frac{3}{2}Q_3, Q_3 = Q_3, Q_2 = \frac{1}{2}Q_3, Q_1 = \frac{1}{3}Q_3$$

(with negligible flow resistances of the other components of the apparatus 300, such as the plurality of valves 310, the inlet conduit 340, and the outlet conduit 350, and with the same pressure differential $\Delta P$ for each state).

In certain embodiments, the apparatus 300 is configured to be provided to a medical professional (e.g., surgeon) with each of the valves of the plurality of valves 330 in a predetermined state (e.g., in a "factory configuration" which has a predetermined "factory" flow rate), and the medical professional can select a desired configuration of the apparatus 300 by selecting and actuating none, one, or more of the valves such that the apparatus 300 is set to provide a selected flow rate (e.g., the same as the "factory" flow rate or different from the "factory" flow rate). In certain embodiments, the apparatus 300 is configured to provide a default minimum flow rate (e.g., greater than zero) when in a configuration in which all of the valves of the plurality of valves 330 are in "closed" states.

In certain embodiments, the plurality of valves 330 comprises one or more check valves, stop-check valves, or other types of valves. In certain embodiments, some or all of the valves of the plurality of valves 330 are configured to be switched multiple times (e.g., reversibly switchable; multiple actuations) between valve states of the valve. For example, at least one valve can be configured to be switched to a second valve state from an initial first valve state, and configured to be subsequently switched back to the first valve state or to another valve state different from the second valve state.

In certain other embodiments, some or all of the valves of the plurality of valves 330 are configured to be switched once (e.g., irreversibly switchable; single actuation) between valve states of the valve. For example, at least one valve can be configured to be switched to a second valve state from an initial first valve state, and configured to not be subsequently switched back to the first valve state or to another valve state different from the second valve state. Examples of valves that are configured to be switched once include, but are not limited to, at least one conduit section configured to be irreversibly compressed (e.g., collapsed; crushed) such that liquid flow through the at least one conduit section is prevented. The conduit section of certain such embodiments is plastically deformable or malleable by localized pressure applied to a wall of the conduit section. The conduit section of certain other such embodiments is resilient and the valve further comprises a plastically deformable or malleable actuator (e.g., plate) configured to be pressed against a wall of the conduit section, causing the actuator to be irreversibly deformed into a configuration which compresses (e.g., collapses; crushes) the conduit section such that liquid flow through the conduit section is prevented. In certain embodiments, the apparatus 300 is configured to be provided to a medical professional (e.g., surgeon) with each of one or more irreversibly switchable valves of the plurality of valves 330 in an "open" state (e.g., such that the apparatus 300 provides the "factory" flow rate), and the medical professional can select a desired configuration of the apparatus 300 by selecting and actuating (e.g., irreversibly closing) none, one, or more of the one or more irreversibly switchable valves such that the apparatus 300 is set to provide a selected flow rate (e.g., the same as the "factory" flow rate or different from the "factory" flow rate).

In certain embodiments, some or all of the valves of the plurality of valves 330 are configured to be manually switched (e.g., by a medical professional manipulating a button or other mechanism mechanically coupled to the actuator of the valve) between the valve states of the valve prior to or during implantation of the apparatus 300 on or within a recipient. For example, in certain other embodiments, some or all of the valves of the plurality of valves 330 are configured to be switched (e.g., by an electromechanical mechanism or motor mechanically coupled to the actuator of the valve) between the valve states of the valve subsequently to implantation of the apparatus 300 (e.g., in response to commands received from a controller circuitry internal or external to the apparatus 300 being used by a medical professional). Examples of valves compatible with certain embodiments described herein include but are not limited to, the at least one valve 204 and accompanying mechanisms as described herein with regard to FIGS. 2A and 2B.

In certain embodiments, the plurality of valves 330 comprises at least one valve having an actuator configured to be moved to change the valve between an open state and a closed state (e.g., referred to herein as a "two-state valve"). For example, the two-state valve can comprise a rotatable actuator mechanically coupled to a valve conduit such that the valve conduit is in fluidic communication with both an inlet valve port and an outlet valve port when the actuator is in a first orientation (e.g., an open orientation) and the valve conduit is not in fluidic communication with one or both of the inlet valve port or the outlet valve port when the actuator is in a second orientation (e.g., a closed orientation) that differs from the first orientation (e.g., by 90 degrees). For another example, the two-state valve can comprise a linearly movable actuator mechanically coupled to a mechanism (e.g., disc and seat; moveable conduit) configured to be switched between a first position (e.g., an open position) in which the mechanism allows liquid flow from the inlet valve port to the outlet valve port and a second position (e.g., a closed position) in which the mechanism prevents liquid flow from the inlet valve port to the outlet valve port.

FIGS. 6A-6D schematically illustrate a two-state first valve 330a and a two-state second valve 330b in accordance with certain embodiments described herein. While FIGS. 6A-6D illustrate the first valve 330a and the second valve 330b as each comprising a rotatable actuator 360a,b mechanically coupled to a valve conduit 362a,b, other types of two-state valves (e.g., linearly actuated valves) are also compatible with certain embodiments described herein. The first valve 330a is configured to be controllably opened and closed to selectively place the inlet port 334 in fluidic communication with the first port 332a (and the inlet portion of the first conduit 310a), and the second valve 330b is configured to be controllably opened and closed to selectively place the inlet port 334 in fluidic communication with the third port 332c (and the inlet portion of the second conduit 310b).

Figure 5C:
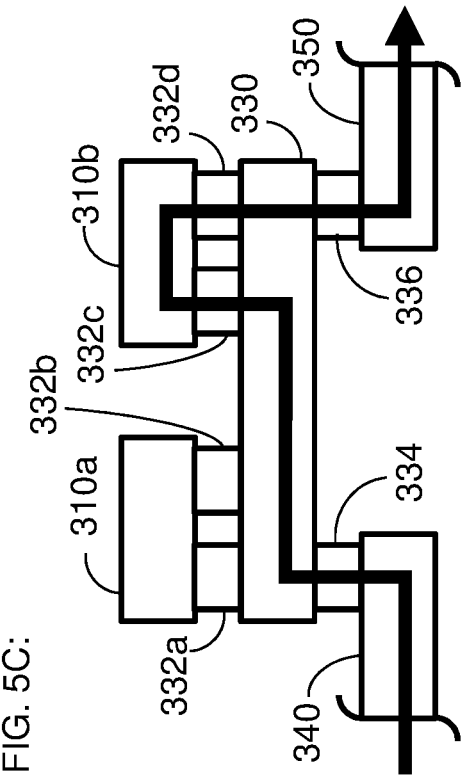
FIGS. 5A-5D schematically illustrate four states of a plurality of states in accordance with certain embodiments described herein.
Figure 5D:
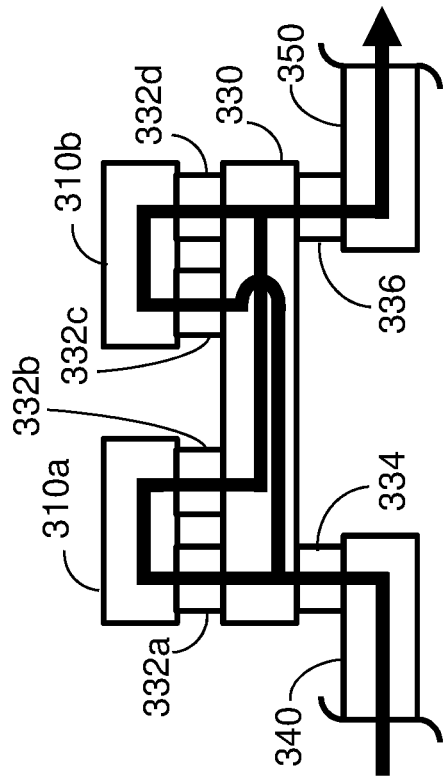
Figure 5A:
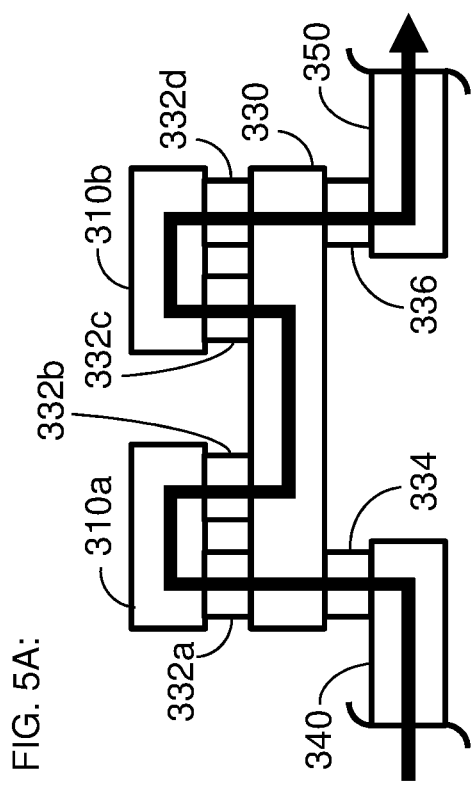
Figure 5B:
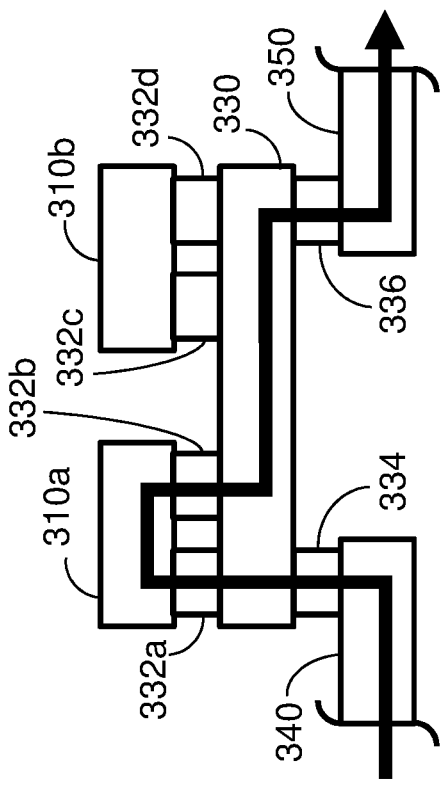
Figure 6C:
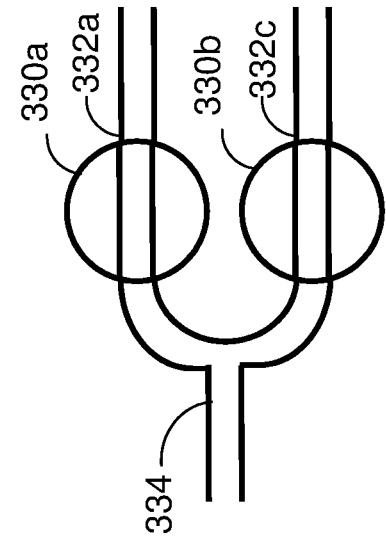
FIGS. 6A-6D schematically illustrate a two-state first valve and a two-state second valve in accordance with certain embodiments described herein.
Figure 6D:
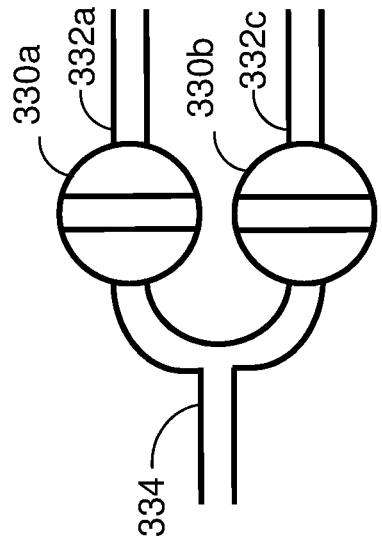
Figure 6A:
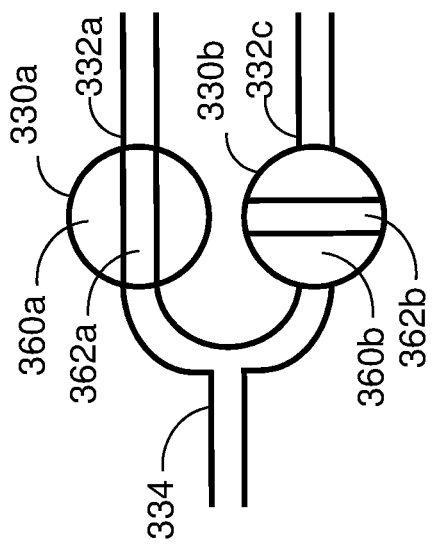
Figure 6B:
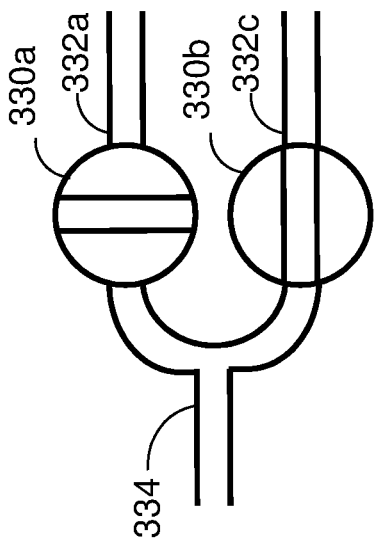

As schematically illustrated by FIG. 6A, the first valve 330a is open and the inlet port 334 is in fluidic communication with the first port 332a, and the second valve 330b is closed and the inlet port 334 is not in fluidic communication with the third port 332c. This configuration of the first valve 330a and the second valve 330b is compatible with the first state of the plurality of valves 330 schematically illustrated by FIG. 5A and with the second state of the plurality of valves 330 schematically illustrated by FIG. 5B. As schematically illustrated by FIG. 6B, the first valve 330a is closed and the inlet port 334 is not in fluidic communication with the first port 332a, and the second valve 330b is open and the inlet port 334 is in fluidic communication with the third port 332c. This configuration of the first valve 330a and the second valve 330b is compatible with the third state of the plurality of valves 330 schematically illustrated by FIG. 5C. As schematically illustrated by FIG. 6C, the first valve 330a is open and the inlet port 334 is in fluidic communication with the first port 332a, and the second valve 330b is open and the inlet port 334 is in fluidic communication with the third port 332c. This configuration of the first valve 330a and the second valve 330b is compatible with the fourth state of the plurality of valves 330 schematically illustrated by FIG. 5D. As schematically illustrated by FIG. 6D, the first valve 330a is closed and the inlet port 334 is not in fluidic communication with the first port 332a, and the second valve 330b is closed and the inlet port 334 is not in fluidic communication with the third port 332c. This configuration of the first valve 330a and the second valve 330b is compatible with a fifth state of the plurality of valves 330 in which the liquid 320 does not flow through either the first conduit 310a or the second conduit 310b.

Figure 7:
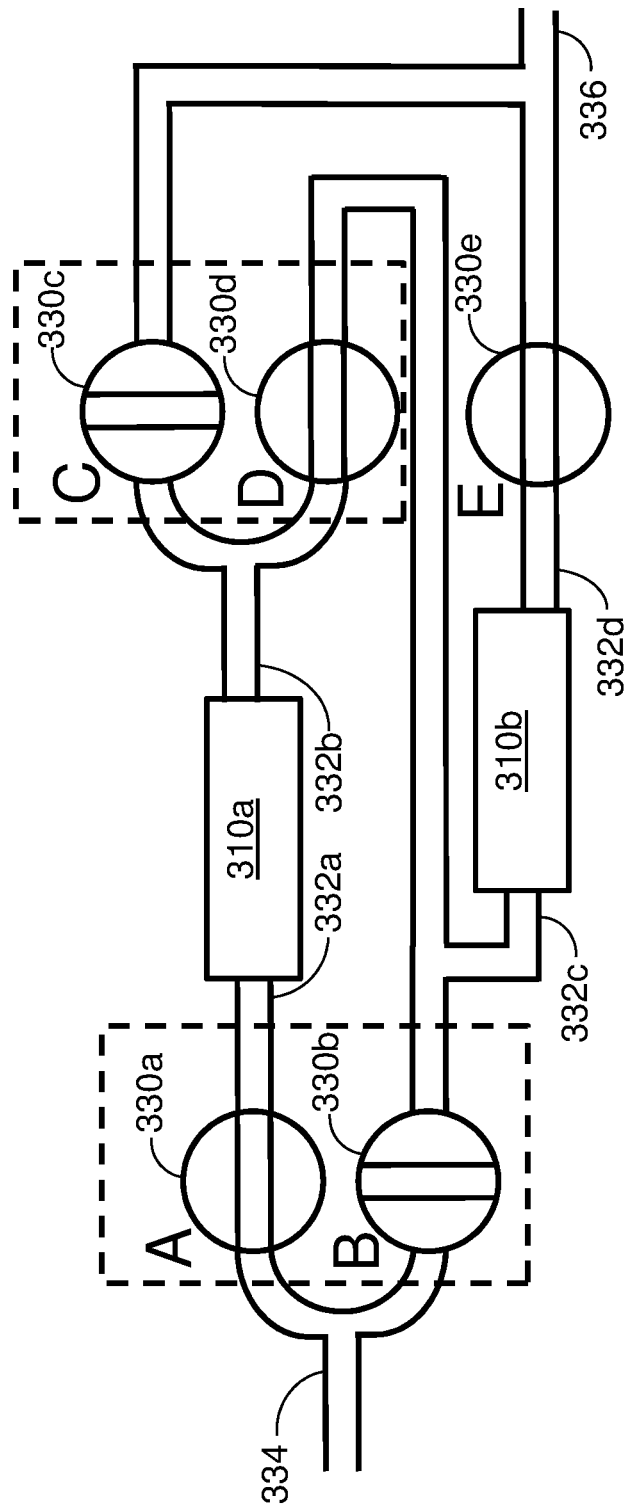
FIG. 7 schematically illustrates an example apparatus having five two-state valves in accordance with certain embodiments described herein FIGS. 8A-8C schematically illustrate an example valve having three valve states in accordance with certain embodiments described herein.

FIG. 7 schematically illustrates an example apparatus 300 having five two-state valves in accordance with certain embodiments described herein. The first valve 330a (labeled "A") and the second valve 330b (labeled "B") are configured as described herein with regard to FIGS. 6A-6D. A third valve 330c (labeled "C") is configured to be controllably opened and closed to selectively place the second port 332b in fluidic communication with the outlet port 336. A fourth valve 330d (labeled "D") is configured to be controllably opened and closed to selectively place the second port 332b in fluidic communication with the third port 332c (and the inlet portion of the second conduit 310b). FIG. 7 also includes a fifth valve 330e (labeled "E") that is configured to be controllably opened and closed to selectively place the fourth port 332d in fluidic communication with the outlet port 336. As described herein, in certain other embodiments, the apparatus 300 does not include a fifth valve 330e. Table 1 provides the states of each of the five two-state valves 330a-e corresponding to the plurality of states schematically illustrated in FIGS. 5A-5D in accordance with certain embodiments described herein.

TABLE 1

|  | Valve A | Valve B | Valve C | Valve D | Valve E |
|---|---|---|---|---|---|
| Slowest fluid flow (FIG. 5A) | Open | Closed | Closed | Open | Open |
| Slow fluid flow (FIG. 5B) | Open | Closed | Open | Closed | Closed |
| Fast fluid flow (FIG. 5C) | Closed | Open | Closed | Closed | Open |
| Fastest fluid flow (FIG. 5D) | Open | Open | Open | Closed | Open |
| No fluid flow | Closed | Closed | — | — | — |

While Table 1 shows that, in certain embodiments, the fifth state of no fluid flow can be achieved by closing the first valve 330a and the second valve 330b (e.g., preventing the liquid 320 from entering the plurality of valves 330), in certain other embodiments, the fifth state can be achieved by instead closing the third valve 330c and the fifth valve 330e (e.g., preventing the liquid 320 from leaving the plurality of valves 330). In certain embodiments, the fifth valve ("Valve E") is not included. For example, in configurations in which back flow through the second conduit 310b is not appreciable, the slow fluid flow state (e.g., as shown in FIG. 5B) can be achieved with Valve E in an "open" state, or without Valve E entirely (e.g., an apparatus 300 having four two-state valves). In some embodiments, Valve E can be a check valve (e.g., a valve that permits flow in one direction from the port 332d to the outlet port 336) that prevents back flow without requiring actuation (e.g., manual or otherwise).

FIGS. 8A-8C schematically illustrate an example valve 330f having three valve states in accordance with certain embodiments described herein. FIGS. 8D-8F schematically illustrate another example valve 330g having three valve states in accordance with certain embodiments described herein. FIGS. 8G-8H schematically illustrate an example valve 330h having two valve states in accordance with certain embodiments described herein. Both of the valves 330f,g are referred to herein as a "three-state valve," and the valve 330h is referred to herein as a two-state valve. While the valves 330f-h are schematically illustrated in FIGS. 8A-8H as having rotatable actuators, other types of three-state valves and two-state valves (e.g., utilizing linear motion actuators) are also compatible with certain embodiments described herein.

The valve 330f of FIGS. 8A-8C has a first valve port (e.g., in fluidic communication with the inlet port 334), a second valve port (e.g., in fluidic communication with the first port 332a), and a third valve port (e.g., in fluidic communication with the third port 332c). The valve 330f is configured to be placed in a selected valve state of a plurality of valve states. In a first valve state of the valve 330f, the first valve port is in fluidic communication with the second valve port and with the third valve port (e.g., such that the inlet port 334 is in fluidic communication with both the first port 332a and the third port 332*c*). In a second valve state of the valve 330*f,* the first valve port is in fluidic communication with the second valve port and is not in fluidic communication with the third valve port (e.g., such that the inlet port 334 is not in fluidic communication with the first port 332*a* and is in fluidic communication with the third port 332*c*). In a third valve state of the valve 330*f,* the first valve port is not in fluidic communication with the second valve port and is in fluidic communication with the third valve port (e.g., such that the inlet port 334 is in fluidic communication with the first port 332*a* and is not in fluidic communication with the third port 332*c*).

The valve 330*g* of FIGS. 8D-8F has a first valve port (e.g., in fluidic communication with the second port 332*b*), a second valve port (e.g., in fluidic communication with the outlet port 336), and a third valve port (e.g., in fluidic communication with the third port 332*c*). The valve 330*g* is configured to be placed in a selected valve state of a plurality of valve states. In a first valve state of the valve 330*g*, the first valve port is in fluidic communication with the second valve port and is not in fluidic communication with the third valve port (e.g., such that the second port 332*b* is in fluidic communication with the outlet port 336 and is not in fluidic communication with the third port 332*c*). In a second valve state of the valve 330*g*, the first valve port is not in fluidic communication with either the second valve port or the third valve port, and the second valve port is not in fluidic communication with the third valve port (e.g., such that the second port 332*b* is not in fluidic communication with either the outlet port 336 or the third port 332*c* and the outlet port 336 is not in fluidic communication with the third port 332*c*). In a third valve state of the valve 330*g*, the first valve port is in fluidic communication with the third valve port and is not in fluidic communication with the second valve port (e.g., such that the second port 332*b* is in fluidic communication with the third port 332*c* and is not in fluidic communication with the outlet port 336).

The valve 330*h* of FIGS. 8G-8H (a two-state valve) has a first valve port (e.g., in fluidic communication with the fourth port 332*d*) and a second valve port (e.g., in fluidic communication with the outlet port 336). The valve 330*h* is configured to be placed in a selected valve state of a plurality of valve states. In a first valve state of the valve 330*h*, the first valve port is in fluidic communication with the second valve port (e.g., such that the fourth port 332*d* is in fluidic communication with the outlet port 336). In a second valve state of the valve 330*h*, the first valve port is not in fluidic communication with the second valve port (e.g., such that the fourth port 332*d* is not in fluidic communication with outlet port 336). In certain embodiments, the valve 330*h* is not included. For example, in configurations in which back flow through the second conduit 310*b* is not appreciable, the slow fluid flow state (e.g., as shown in FIG. 5B) can be achieved with the valve 330*h* in an "open" state, or without the valve 330*h* entirely (e.g., an apparatus 300 having only the two three-state valves 330*f,g*).

In certain embodiments, the three-state valve 330*f* of FIGS. 8A-8C is used in place of the two two-state valves 330*a,b* (labeled A and B) of FIG. 7 and/or the three-state valve 330*g* is used in place of the two two-state valves 330*c,d* (labeled C and D) of FIG. 7. Other valves with different numbers of valve states and other configurations of the plurality of valves 300 are also compatible with certain embodiments described herein.

FIG. 9A-9D schematically illustrates an example pair of valves 330*i,j* having a common actuator 380 configured to be moved linearly to change a valve state of each of the two valves 330*i,j* in accordance with certain embodiments described herein. The actuator 380 of FIGS. 9A-9D comprises an elongate member 382 configured to be moved linearly within a valve body 390 having four valve ports 392*a,b,c,d*. The elongate member 382 comprises at least one recess 384 (e.g., hole; narrow portion) configured to allow liquid flow across or through the elongate member 380. For example, in FIGS. 9A-9D, the at least one recess 384 comprises a first recess 384*a* and a second recess 384*b* spaced apart from one another along the elongate member 382. The elongate member 382 further comprises at least one portion 386 configured to prevent liquid flow across or through the elongate member 382.

FIG. 9A schematically illustrates a first valve state in which the elongate member 382 is positioned such that the valve 330*i* is open (e.g., the two valve ports 392*a,b* are in fluidic communication with one another via the recess 384*a*), and the valve 330*j* is closed (e.g., the two valve ports 392*c,d* are not in fluidic communication with one another). FIG. 9B schematically illustrates a second valve state in which the elongate member 382 is positioned such that the valve 330*i* is open (e.g., the two valve ports 392*a,b* are in fluidic communication with one another via the recess 384*b*) and the valve 330*j* is open (e.g., the two valve ports 392*c,d* are in fluidic communication with one another via the recess 382*a*). FIG. 9C schematically illustrates a third valve state in which the elongate member 382 is positioned such that the valve 330*i* is closed (e.g., the two valve ports 392*a,b* are not in fluidic communication with one another) and the valve 330*j* is closed (e.g., the two valve ports 392*c,d* are not in fluidic communication with one another). FIG. 9D schematically illustrates a fourth valve state in which the elongate member 382 is positioned such that the valve 330*i* is closed (e.g., the two valve ports 392*a,b* are not in fluidic communication with one another) and the valve 330*j* is open (e.g., the two valve ports 392*c,d* are in fluidic communication with one another via the recess 384*b*). In certain embodiments, a pair of valves 330*i,j* as schematically illustrated by FIGS. 9A-9D are used in place of the two valves 330*a,b* (labeled A and B) of FIG. 7 and/or in place of the two valves 330*c,d* (labeled C and D) of FIG. 7.

FIG. 10 schematically illustrates an example plurality of valves 330 comprising five valves with a common linear actuator 380 in accordance with certain embodiments described herein. The elongate member 382 comprises a plurality of recesses 384 and a plurality of portions 386 arranged along the elongate member 382 such that the state of the plurality of valves 330 is set by linearly translating the elongate member 382 to align the recesses 384 and portions 386 appropriately with the ports of the plurality of valves 330.

For a first flow rate (e.g., the fastest flow rate), the elongate member 382 is positioned such that the plurality of valves 330 allows flow of the liquid 320 through the first conduit 310*a* and the second conduit 310*b* in parallel with one another. For a second flow rate (e.g., the fast flow rate), the elongate member 382 is positioned such that the plurality of valves 330 allows flow of the liquid 320 through the second conduit 310*b* but not the first conduit 310*a*. For a third flow rate (e.g., the slow flow rate), the elongate member 382 is positioned such that the plurality of valves 330 allows flow of the liquid 320 through the first conduit 310*a* but not the second conduit 310*b*. For a fourth flow rate (e.g., the slowest flow rate), the elongate member 382 is positioned such that the plurality of valves 330 allows flow of the liquid 320 through the first conduit 310*a* and the second conduit 310*b* in series with one another.

As schematically illustrated in FIG. 10, the sections of the elongate member 382 corresponding to the different flow rates can be arranged such that the state of the plurality of valves 330 can be changed by moving the elongate member 382 by discrete steps along an axial direction of the elongate member 382, the discrete steps equal to the spacings between the adjacent recesses 384 and portions 386. For example, if the elongate member 382 is initially positioned such that the plurality of valves 330 is in the third state (e.g., the "fast" flow rate), switching to the second state (e.g., the "slow" flow rate) can be achieved by moving the elongate member 382 by 2 discrete steps, switching to the first state (e.g., the "slowest" flow rate) can be achieved by moving the elongate member 382 by 5 discrete steps, and switching to the fourth state (e.g., the "fastest" flow rate) can be achieved by moving the elongate member 382 by 9 discrete steps. Certain such embodiments are conducive to remote activation of the plurality of valves 330 (e.g., by a single linear motion motor).

Figure 11:
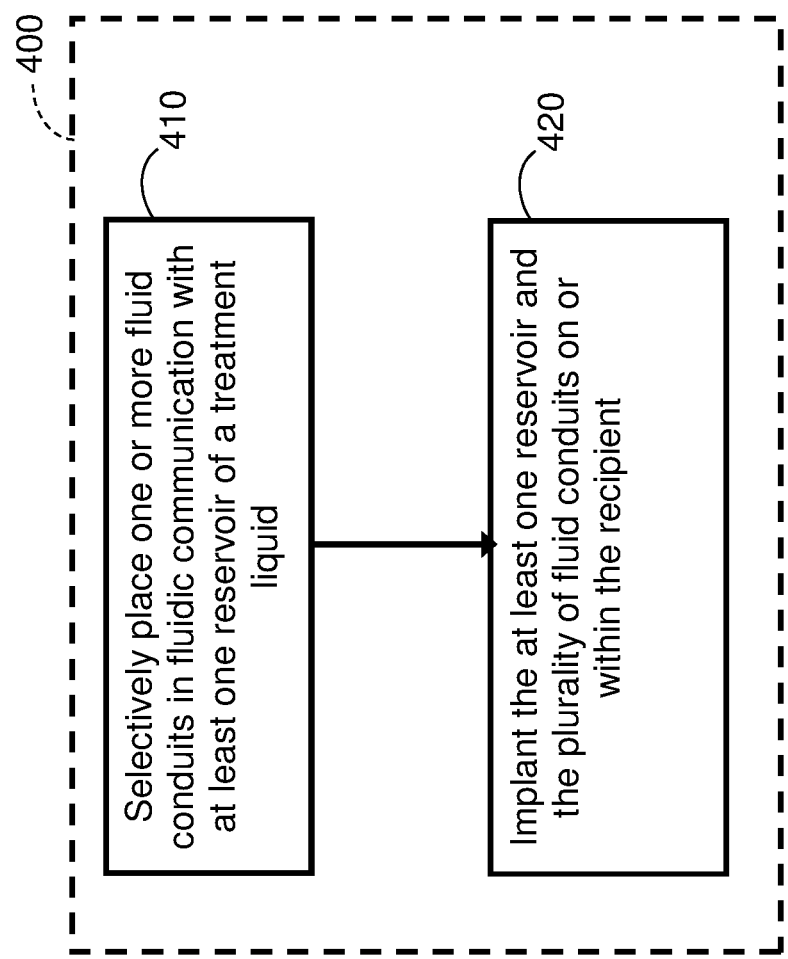
FIG. 11 is a flow diagram of an example method in accordance with certain embodiments described herein.

FIG. 11 is a flow diagram of an example method 400 in accordance with certain embodiments described herein. In an operational block 410, the method 400 comprises selectively placing one or more fluid conduits of a plurality of fluid conduits (e.g., a plurality of conduits 310; a plurality of flow restrictors) in fluidic communication with at least one reservoir of a treatment liquid (e.g., a reservoir 202 containing a liquid 420 comprising at least one treatment substance). The at least one reservoir is configured to be implanted on or within a recipient. The one or more fluid conduits are selected, at least in part, to provide a predetermined flow rate of the treatment liquid to the recipient. In an operational block 420, the method 400 further comprises implanting the at least one reservoir and the plurality of fluid conduits on or within the recipient. In certain embodiments, the method 400 further comprises allowing the treatment liquid to flow from the at least one reservoir through the selected one or more fluid conduits to administer the treatment liquid to the recipient.

In certain embodiments, the at least one reservoir and the plurality of fluid conduits are contained within a housing configured to be implanted on or within the recipient. For example, the housing can be formed of a biocompatible material (e.g., silicone; thermoplastic polymer resin, thermoplastic elastomer; platinum; platinum alloy; titanium; titanium alloy) and the housing can hermetically seal an inner region of the housing from an outer environment of the housing. In certain embodiments, the housing also contains a flow control system in fluidic communication with the at least one reservoir and the plurality of fluid conduits. For example, the flow control system can comprise at least one input port (e.g., inlet conduit 340 and inlet port 334) configured to receive the treatment liquid from the at least one reservoir, and at least one output port (e.g., outlet port 336 and outlet conduit 350) configured to administer the treatment liquid internally to the recipient. The flow control system of certain embodiments further comprises a plurality of valves (e.g., a plurality of valves 330) in fluidic communication with the plurality of fluid conduits. The plurality of valves are configured to controllably allow flow from the at least one input port, through a selected set of the fluid conduits, to the at least one output port.

In certain embodiments, the one or more fluid conduits are selected prior to said implanting of the at least one reservoir and the plurality of fluid conduits. For example, the apparatus can be shipped from the manufacturer with the plurality of valves in a selected state corresponding to the predetermined flow rate of the treatment liquid. For another example, the apparatus can be adjusted (e.g., by a surgeon or other health professional) prior to the surgical implantation procedure to modify the plurality of valves to be in a selected state corresponding to the predetermined flow rate of the treatment liquid. In certain other embodiments, the one or more fluid conduits are selected during said implanting. For example, the apparatus can be adjusted (e.g., by a surgeon or other health professional) during the surgical implantation procedure to modify the plurality of valves to be in a selected state corresponding to the predetermined flow rate of the treatment liquid.

In certain embodiments, the one or more fluid conduits are selected subsequently to said implanting of the at least one reservoir and the plurality of fluid conduits. For example, the apparatus can be adjusted remotely (e.g., by a health professional, clinician, or caregiver) by sending appropriate signals to an internal electromechanical mechanism (e.g., motor) of the apparatus. In certain embodiments, the method 400 further comprises changing the flow rate of the treatment liquid to the recipient by changing the selected one or more fluid conduits that are in fluidic communication with the at least one reservoir subsequently to said implanting (e.g., by adjusting the apparatus remotely using an internal electromechanical mechanism (e.g., motor) of the apparatus.

It is to be appreciated that the embodiments disclosed herein are not mutually exclusive and may be combined with one another in various arrangements.

The invention described and claimed herein is not to be limited in scope by the specific example embodiments herein disclosed, since these embodiments are intended as illustrations, and not limitations, of several aspects of the invention. Any equivalent embodiments are intended to be within the scope of this invention. Indeed, various modifications of the invention in form and detail, in addition to those shown and described herein, will become apparent to those skilled in the art from the foregoing description. Such modifications are also intended to fall within the scope of the claims. The breadth and scope of the invention should not be limited by any of the example embodiments disclosed herein, but should be defined only in accordance with the claims and their equivalents.

What is claimed is:

1. An apparatus comprising:
    a plurality of conduits configured to receive liquid from at least one liquid reservoir configured to be implanted on or within a recipient, each conduit of the plurality of conduits having a corresponding flow resistance to the liquid, the plurality of conduits comprises a first conduit having a first flow resistance and a second conduit having a second flow resistance lower than the first flow resistance; and
    a plurality of valves in fluidic communication with the plurality of conduits, the plurality of valves configured to controllably allow flow of the liquid through a selected set of the conduits to be administered internally to the recipient with a selected flow rate, the plurality of valves configured to be placed in a selected state of a plurality of states comprising:
        a first state in which the plurality of valves allows flow of the liquid through the first conduit and the second conduit in series with one another;
        a second state in which the plurality of valves allows flow of the liquid through the first conduit and does not allow flow of the liquid through the second conduit;

a third state in which the plurality of valves allows flow of the liquid through the second conduit and does not allow flow of the liquid through the first conduit; and a fourth state in which the plurality of valves allows flow of the liquid through the first conduit and the second conduit in parallel with one another.

2. The apparatus of claim 1, wherein the plurality of states further comprises a fifth state in which the plurality of valves does not allow flow of the liquid through either the first conduit or the second conduit.

3. The apparatus of claim 1, wherein the plurality of valves comprises at least one valve having an actuator configured to be moved linearly to change the at least one valve between states.

4. The apparatus of claim 3, wherein the plurality of valves comprises at least two valves having a common actuator configured to be moved linearly to change a valve state of each of the at least two valves.

5. The apparatus of claim 1, wherein the plurality of valves comprises at least one valve having an actuator configured to be rotated to change the at least one valve between states.

6. The apparatus of claim 1, further comprising:
a housing configured to be implanted on or within a recipient; and
the at least one liquid reservoir within the housing, the at least one liquid reservoir configured to contain the liquid; and
wherein the plurality of conduits and the plurality of valves are components of a flow control system within the housing, the flow control system comprising:
at least one input port configured to receive the liquid from the at least one liquid reservoir; and
at least one output port configured to administer the liquid internally to the recipient.

7. The apparatus of claim 1, wherein the first flow resistance is equal to twice the second flow resistance.

8. The apparatus of claim 1, wherein the plurality of valves comprises at least one two-state valve configured to be switched between an open state and a closed state.

9. The apparatus of claim 1, wherein the plurality of valves comprises at least one two-state valve configured to be switched between an open state and a closed state and a single linearly movable actuator configured to switch a valve state of each two-state valve of the plurality of valves.

10. The apparatus of claim 1, further configured to be implanted within a recipient.

11. The apparatus of claim 1, wherein at least one valve of the plurality of valves is configured to be switched once between valve states to provide the selected flow rate.

12. The apparatus of claim 1, wherein the plurality of valves is configured to be placed in a selected state of a plurality of states, the plurality of states comprising a state in which the plurality of valves allows flow of the liquid through at least two conduits of the plurality of conduits in series with one another.

13. An apparatus comprising:
a plurality of conduits configured to receive liquid from at least one liquid reservoir configured to be implanted on or within a recipient, each conduit of the plurality of conduits having a corresponding flow resistance to the liquid; and
a plurality of valves in fluidic communication with the plurality of conduits, the plurality of valves configured to controllably allow flow of the liquid through a selected set of the conduits to be administered internally to the recipient with a selected flow rate, wherein the plurality of valves comprises at least one valve having a first valve port, a second valve port, and a third valve port, the at least one valve configured to be placed in a selected valve state of a plurality of valve states comprising:
a first valve state in which the first valve port is in fluidic communication with the second valve port and the third valve port;
a second valve state in which the first valve port is in fluidic communication with the second valve port and not in fluidic communication with the third valve port; and
a third valve state in which the first valve port is in fluidic communication with the third valve port and not in fluidic communication with the second valve port.

14. The apparatus of claim 13, wherein the plurality of conduits comprises an inlet port configured to receive the fluid from the at least one liquid reservoir and an outlet port configured to administer the liquid to a target region of the recipient.

15. The apparatus of claim 13, wherein some or all of the valves of the plurality of valves are configured to be irreversibly switched.

16. The apparatus of claim 13, wherein some or all of the valves of the plurality of valves are configured to be reversibly switched.

17. An apparatus comprising:
a plurality of conduits configured to receive liquid from at least one liquid reservoir configured to be implanted on or within a recipient, each conduit of the plurality of conduits having a corresponding flow resistance to the liquid; and
a plurality of valves in fluidic communication with the plurality of conduits, the plurality of valves configured to controllably allow flow of the liquid through a selected set of the conduits to be administered internally to the recipient with a selected flow rate, wherein the plurality of valves comprises at least one valve having a first valve port, a second valve port, and a third valve port, the at least one valve configured to be placed in a selected valve state of a plurality of valve states comprising:
a first valve state in which the first valve port is in fluidic communication with the second valve port and is not in fluidic communication with the third valve port;
a second valve state in which the first valve port is not in fluidic communication with either the second valve port or the third valve port, and the second valve port is not in fluidic communication with the third valve port; and
a third valve state in which the first valve port is in fluidic communication with the third valve port and is not in fluidic communication with the second valve port.

18. The apparatus of claim 17, wherein the plurality of conduits comprises an inlet port configured to receive the fluid from the at least one liquid reservoir and an outlet port configured to administer the liquid to a target region of the recipient.

19. The apparatus of claim 17, wherein some or all of the valves of the plurality of valves are configured to be irreversibly switched.

20. The apparatus of claim 17, wherein some or all of the valves of the plurality of valves are configured to be reversibly switched.

21. An apparatus comprising:
a plurality of conduits configured to receive liquid from at least one liquid reservoir configured to be implanted on or within a recipient, each conduit of the plurality of conduits having a corresponding flow resistance to the liquid; and
a plurality of valves in fluidic communication with the plurality of conduits, the plurality of valves configured to controllably allow flow of the liquid through a selected set of the conduits to be administered internally to the recipient with a selected flow rate, wherein the plurality of valves comprises at least one three-state valve having first, second, and third valve ports, the at least one three-state valve having a rotatable actuator configured to be switched between a first actuator state in which the first valve port is in fluidic communication with the second valve port and the third valve port, a second actuator state in which the first valve port is in fluidic communication with the second valve port but not the third valve port, and a third actuator state in which the first valve port is in fluidic communication with the third valve port but not the second valve port.

22. The apparatus of claim 21, further comprising the at least one liquid reservoir, wherein the at least one liquid reservoir is configured to have a first shape during implantation and a second shape after implantation.

23. The apparatus of claim 21, further comprising the at least one liquid reservoir, wherein the at least one liquid reservoir comprises a needle port configured to be refilled by a needle injection through the recipient's skin.

24. An apparatus comprising:
a plurality of conduits configured to receive liquid from at least one liquid reservoir configured to be implanted on or within a recipient, each conduit of the plurality of conduits having a corresponding flow resistance to the liquid; and
a plurality of valves in fluidic communication with the plurality of conduits, the plurality of valves configured to controllably allow flow of the liquid through a selected set of the conduits to be administered internally to the recipient with a selected flow rate, wherein the plurality of valves comprises at least one three-state valve having first, second, and third valve ports, the at least one three-state valve having a rotatable actuator configured to be switched between a first actuator state in which the first valve port is in fluidic communication with the second valve port but not the third valve port, a second actuator state in which the first valve port is in fluidic communication with the third valve port but not the second valve port, and a third actuator state in which the first valve port is not in fluidic communication with either the second valve port or the third valve port.

25. The apparatus of claim 24, further comprising the at least one liquid reservoir, wherein the at least one liquid reservoir is configured to have a first shape during implantation and a second shape after implantation.

26. The apparatus of claim 24, further comprising the at least one liquid reservoir, wherein the at least one liquid reservoir comprises a needle port configured to be refilled by a needle injection through the recipient's skin.

27. An apparatus comprising:
a plurality of conduits configured to receive liquid from at least one liquid reservoir configured to be implanted on or within a recipient, each conduit of the plurality of conduits having a corresponding flow resistance to the liquid; and
a plurality of valves in fluidic communication with the plurality of conduits, the plurality of valves configured to controllably allow flow of the liquid through a selected set of the conduits to be administered internally to the recipient with a selected flow rate, the plurality of valves comprising at least one two-state valve configured to be switched between an open state and a closed state and a single linearly movable actuator configured to switch a valve state of each two-state valve of the plurality of valves, wherein the linearly movable actuator comprises a recess configured to be positioned among at least a first two-state valve and a second two-state valve of the plurality of valves.

28. The apparatus of claim 27, wherein, when the linearly movable actuator is at a first position, the first two-state valve is open via the recess, and wherein, when the linearly movable actuator is at a second position, the second two-state valve is open via the recess.

29. The apparatus of claim 28, wherein, when the linearly movable actuator is at the first position, the second two-state valve is closed, and wherein, when the linearly movable actuator is at the second position, the first two-state valve is closed.

30. The apparatus of claim 27, wherein the plurality of valves comprises five two-state valves which are switched by the linearly movable actuator.

* * * * *